(12) United States Patent
Gutke et al.

(10) Patent No.: US 8,461,120 B2
(45) Date of Patent: Jun. 11, 2013

(54) MACROCYCLIC COMPOUNDS POUNDS AND METHODS OF USE THEREOF

(75) Inventors: Hans-Jurgen Gutke, Stuttgart (DE); Michael Burnet, Kusterdingen (DE); Jan-Hinrich Guse, Tubingen-Buhl (DE)

(73) Assignee: Synovo GmbH, Tubingen (DE)

( * ) Notice: Subject to any disclaimer, the term of this patent is extended or adjusted under 35 U.S.C. 154(b) by 0 days.

(21) Appl. No.: 12/847,740

(22) Filed: Jul. 30, 2010

(65) Prior Publication Data

US 2011/0028417 A1    Feb. 3, 2011

Related U.S. Application Data

(63) Continuation of application No. 11/241,514, filed on Sep. 30, 2005, now Pat. No. 7,767,797.

(60) Provisional application No. 60/614,260, filed on Sep. 30, 2004, provisional application No. 60/615,876, filed on Oct. 6, 2004, provisional application No. 60/635,512, filed on Dec. 14, 2004.

(51) Int. Cl.
*A61K 31/70* (2006.01)
*C07H 17/08* (2006.01)

(52) U.S. Cl.
USPC ................. 514/29; 536/7.2; 536/7.3; 536/7.4

(58) Field of Classification Search
USPC .................................................... 536/7.2, 7.4
See application file for complete search history.

(56) References Cited

U.S. PATENT DOCUMENTS

| | | | |
|---|---|---|---|
| 3,928,387 A | 12/1975 | Kierstead et al. | |
| 6,342,590 B1 * | 1/2002 | Morimoto et al. | 536/7.4 |
| 6,420,536 B1 * | 7/2002 | Bronk et al. | 536/7.4 |
| 6,600,025 B1 * | 7/2003 | Lee et al. | 536/7.3 |
| 6,727,352 B2 * | 4/2004 | Cheng et al. | 536/7.4 |
| 6,777,393 B2 | 8/2004 | Bronk et al. | |
| 6,933,283 B2 * | 8/2005 | Clark et al. | 514/29 |
| 7,767,797 B1 | 8/2010 | Gutke et al. | |
| 2004/0087517 A1 | 5/2004 | Burnet et al. | |
| 2004/0186063 A1 | 9/2004 | Gutke et al. | |
| 2005/0171342 A1 | 8/2005 | Burnet et al. | |
| 2006/0099660 A1 | 5/2006 | Burnet et al. | |
| 2008/0145343 A1 | 6/2008 | Burnet et al. | |

FOREIGN PATENT DOCUMENTS

| | | |
|---|---|---|
| WO | WO-03/070173 | 8/2003 |
| WO | WO-03/070174 | 8/2003 |
| WO | WO-2005/027828 | 3/2005 |

* cited by examiner

*Primary Examiner* — Elli Peselev
(74) *Attorney, Agent, or Firm* — Edwards Wildman Palmer LLP; Jeffrey D. Hsi; Mark D. Russett

(57) ABSTRACT

The invention features novel macrocyclic compounds, methods of making the compounds, pharmaceutical compositions including the compounds, and methods of treatment using the compounds.

3 Claims, 2 Drawing Sheets

Figure 1.    Compound A          Compound B
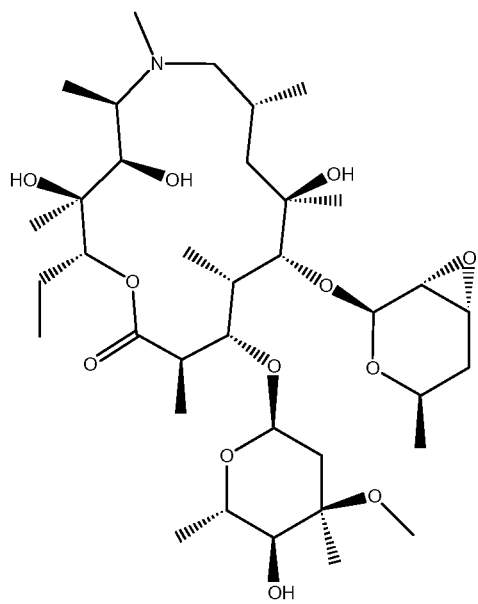 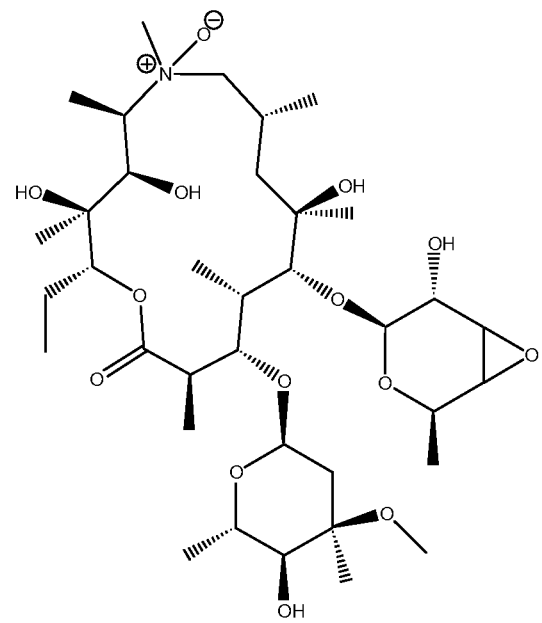

MACROCYCLIC COMPOUNDS POUNDS AND METHODS OF USE THEREOF

CROSS-REFERENCE TO RELATED APPLICATIONS

This application is a continuation of U.S. patent application Ser. No. 11/241,514, filed Sep. 30, 2005, now U.S. Pat. No. 7,767,797, which claims the benefit of priority to U.S. provisional patent application Ser. No. 60/614,260, filed Sep. 30, 2004; Ser. No. 60/615,876, filed Oct. 6, 2004; and Ser. No. 60/635,512, filed Dec. 14, 2004 now abandoned. The contents of each of these applications are incorporated herein by reference in their entirety.

BACKGROUND

Macrocyclic lactones, and in particular, the "azalides" are semi-synthetic compounds with a range of biological activities. Amongst the best known of these is antibiotic activity through binding to the bacterial ribosome. The compounds do, however, have a range of other activities including anti-inflammatory activity (see, e.g., EP0283055). In recent years, it has been proposed that macrocycles may have broader application as drug carriers in which an active substance is reversibly bonded to the macrocycle via an ester bond (see, e.g., PCT 03/070174).

Various observations have linked the anti-bacterial activity of macrolides to the interaction between the hydroxyl group on the desosamine ring and the bacterial ribosome. Modification of this position on the macrolide, should, therefore, reduce anti-biotic activity while providing for alternative interactions with other target proteins.

A large number of researchers have reported derivatives with variation in this part of the molecule including Kobrehel et al. Also reported are substitutions on the macrolactone ring or modification of the sugar residues (for example, cladinose to carbonyl in the case of the ketolides). However, the majority of this work has been performed with the objective of designing new molecules having antibiotic activity.

SUMMARY OF THE INVENTION

This invention relates to novel, semisynthetic macrocycles related to erythromycin or the azalide series or compounds, particularly to derivatives of erythromycin and azithromycin, and to pharmaceutically acceptable addition salts thereof, to a process and intermediates for the preparation thereof, and to their use in the preparation of pharmaceuticals for the treatment of inflammations, neoplasms, cardiovascular diseases metabolic diseases and infections amongst other disease areas.

In one aspect, the invention provides a compound represented by the structure:

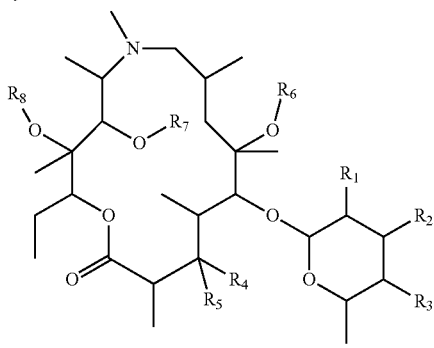

wherein:
$R^1$=OH, O-acyl, $N_3$, $NH_2NH_2$, $NR_2$, in which R is independently for each occurrence H, alkyl, aryl, or heteroaryl;
$R^2$=OH, O-acyl, $NR_2$, in which R is independently for each occurrence H, alkyl, aryl, or heteroaryl;
$R^3$=H, OH, O-alkyl, O-acyl
$R^4$=H
$R^5$=cladinosyl, OH, or $R^4$, $R^5$ is =O
$R^6$=H, methyl,
$R^7$, $R^8$=H, acyl, or $R^7$, $R^8$=CO (cyclic carbonate); or a pharmaceutically acceptable salt thereof;
with the proviso that the compound is not azithromycin.

In another aspect, the invention provides a compound represented by the formula:

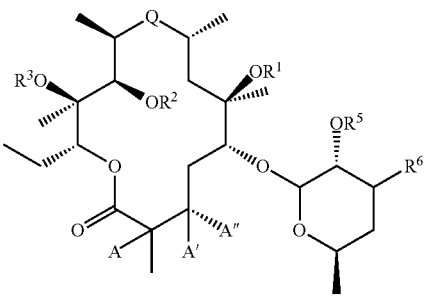

wherein
A and A' are each hydrogen or taken together form a double bond, and A" is H or OH or O-Cladinosyl;
or A=Hydrogen and A' and A" taken together represent =O;
$R^1$, $R^2$, $R^3$, and $R^5$ are independently selected from the group consisting of H, alkyl, acyl, allyl, vinyl, $SiR'_3$ in which R' is, independently for each occurrence, alkyl or aryl);
$R^2$, $R^3$ may be C=O (cyclic carbonate);
$R^6$=H, OH, CN, $N_3$, $NR^8_2$ (in which each $R^8$ is independently H, alkyl or cycloalkyl), alkyl, cycloalkyl, —N(CH$_3$)R$^{8'}$ (in which R$^{8'}$ is H, alkyl, aryl, heteroaryl), or $SR^9$ (in which $R^9$ is H, alkyl or cycloalkyl);
Q=—(C=O)— or —(C=NY)— or —N(CH$_3$)—CH$_2$— or —N(Y)—CH$_2$—, or —CH$_2$—N(Y)—,
wherein Y=H, alkyl, aryl, heteroalkyl, heteroaryl, allyl, alkylheteroaryl, O-Alkyl or O-aryl;
or a pharmaceutically acceptable salt thereof.

In another aspect, the invention provides a compound represented by the structure (Formula I):

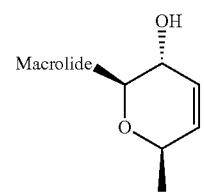

in which Macrolide is a macrocylic macrolide moiety selected from the group consisting of macrolides, macrolactones and azalides.

In another aspect, the invention provides a method of making a compound of Formula I, the method comprising heating a 3-N',N'-dialkyl-amino N' oxide desosamine macrolide compound under conditions such that a 3',4'-olefinic macrolide (more preferably an azalide) is formed.

In another aspect, the invention provides a compound represented by the structure (Formula II):

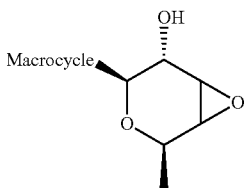

in which Macrolide is a macrolide moiety selected from the group consisting of macrolides, macrolactones and azalides. In preferred embodiments, the compound is represented by the structure:

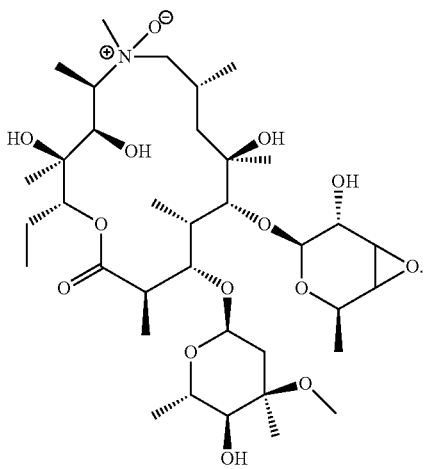 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C3OC3[C@H]2O)[C@](C)(O)C[C@@H](C)C[N+](C)([O-])[C@H](C)[C@@H](O)[C@]1(C)O]

In another aspect, the invention provides a method of making a compound of Formula II, the method including the step of treating a 3',4'-olefinic desosamino compound with an epoxidizing reagent under conditions such that the compound of Formula II is prepared.

In another aspect, the invention provides a method for purifying a 2',3'-epoxy macrolide. The method includes the steps of a) providing the 2',3'-epoxy macrolide; b) contacting the 2',3'-epoxy macrolide with an aqueous solvent and a base under conditions such that the 2',3'-epoxy macrolide precipitates; and c) collecting the precipitated 2',3'-epoxy macrolide. In preferred embodiments, the macrolide is an azalide. In preferred embodiments, the method includes the further step of recrystallizing the precipitated 2',3'-epoxy macrolide.

In another aspect, the invention provides a pharmaceutical composition comprising a compound of claim Formula III herein, or a pharmaceutically acceptable salt thereof, together with a pharmaceutically acceptable excipient.

(Formula III)

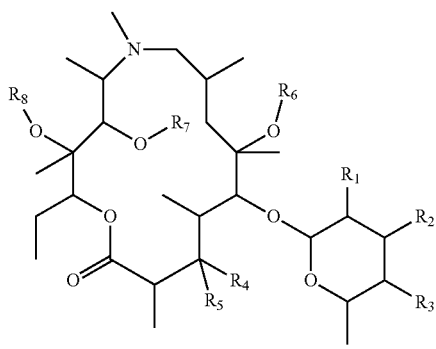

In Formula III, $R^1$=OH, O-acyl, $N_3$, $NH_2NH_2$, $NR_2$ (in which both R residues can independently mean: H, alkyl, aryl, or heteroaryl);

$R^2$=OH, O-acyl, $NR_2$ (in which both R residues can independently mean: H, alkyl, aryl, or heteroaryl);

or $R^1$ and $R^2$ may independently represent more complex residues, for example mono- or oligofunctional moieties (polyamines, bicyclic systems, peptides amines, halogenides, sulphonic esters, acetals, esters, aldehydes, sulfones, sulfonamides, lactones, boronates, silicates, hydroxylamines, alcohols or any type of heterocycle such as imidazoles, thiazoles pyrimidines and combinations thereof), pharmacophores (e.g. sterols, hormones, peptide analogs, nucleosides, anti-inflammatory structures, protease inhibitors, kinase inhibitors) or specifically reactive functions (hydrazines, amino groups, 1,3-dicarbonyl or carboxyl groups, bromoalkyl and bromoaryl groups) that may be conveniently reacted with reagents to form heterocyclic residues or cyclic or heterocyclic assemblies);

$R^3$=H, OH, O-alkyl, O-acyl $R^4$=H $R^5$=cladinosyl, OH, or $R^4$, $R^5$ is =O $R^6$=H, methyl, $R^7$, $R^8$=H, acyl, or $R^7$, $R^8$=CO (cyclic carbonate);

with the proviso that the compound is not azithromycin;

or a pharmaceutically acceptable salt thereof.

In still another aspect, the invention provides a pharmaceutical composition comprising a compound of claim Formula X herein, or a pharmaceutically acceptable salt thereof, together with a pharmaceutically acceptable excipient.

(Formula X)

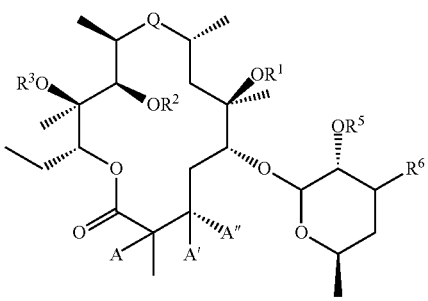

In Formula X, A and A' are Hydrogen or taken together form a double bond and A" is H or OH or O-Cladinosyl;

or A=Hydrogen and A' and A" taken together represent =O;

$R^1$-$R^3$, and $R^5$ are independently H, alkyl, acyl, allyl, vinyl, $SiR_3$ (R in this context may be alkyl or a combination of alkyl and aryl)

$R^2$, $R^3$ may be C=O (cyclic carbonate);

$R^6$=H, OH, CN, $N_3$, $NR^8_2$ ($R^8$ in this context may be, e.g., H or alkyl or cycloalkyl), alkyl, cycloalkyl, —N(CH$_3$)$R^8$ ($R^8$ in this context may be, e.g., H, alkyl, aryl, or heteroaryl; however, it will be understood by the skilled artisan that more complex residues may be represented by this position, for example mono- or oligofunctional moieties or even pharmacophores or otherwise a desired activity causing assembly of chemical building blocks), or $SR^9$ ($R^9$ in this context may be H or alkyl or cycloalkyl);

Q=—(C=O)— or —(C=NY)— or —N(CH$_3$)—CH$_2$— or —N(Y)—CH$_2$—, or —CH$_2$—N(Y)— where Y=H, alkyl, aryl, heteroalkyl, heteroaryl, allyl or alkylheteroaryl or O-Alkyl or O-aryl;

or a pharmaceutically acceptable salt thereof.

In yet another aspect, the invention provides a method of treating an inflammatory, viral, bacterial, cardio-vascular modulators, metabolic or immune disorder. The method includes administering to a subject in need thereof an effective amount of a compound of Formula III herein, such that the inflammatory, viral, bacterial, cardio-vascular modulators, metabolic or immune disorder is treated.

In yet another aspect, the invention provides a method of treating an inflammatory, viral, bacterial, cardio-vascular modulators, metabolic or immune disorder. The method includes administering to a subject in need thereof an effective amount of a compound of Formula X herein, such that the inflammatory, viral, bacterial, cardio-vascular modulators, metabolic or immune disorder is treated.

Other advantages, objects, and features of the invention will be apparent from the description and drawings, and from the claims.

BRIEF DESCRIPTION OF DRAWINGS

FIG. 1 shows the structure of certain compounds of the invention (Compound A and Compound B).

DETAILED DESCRIPTION

Figure 2:
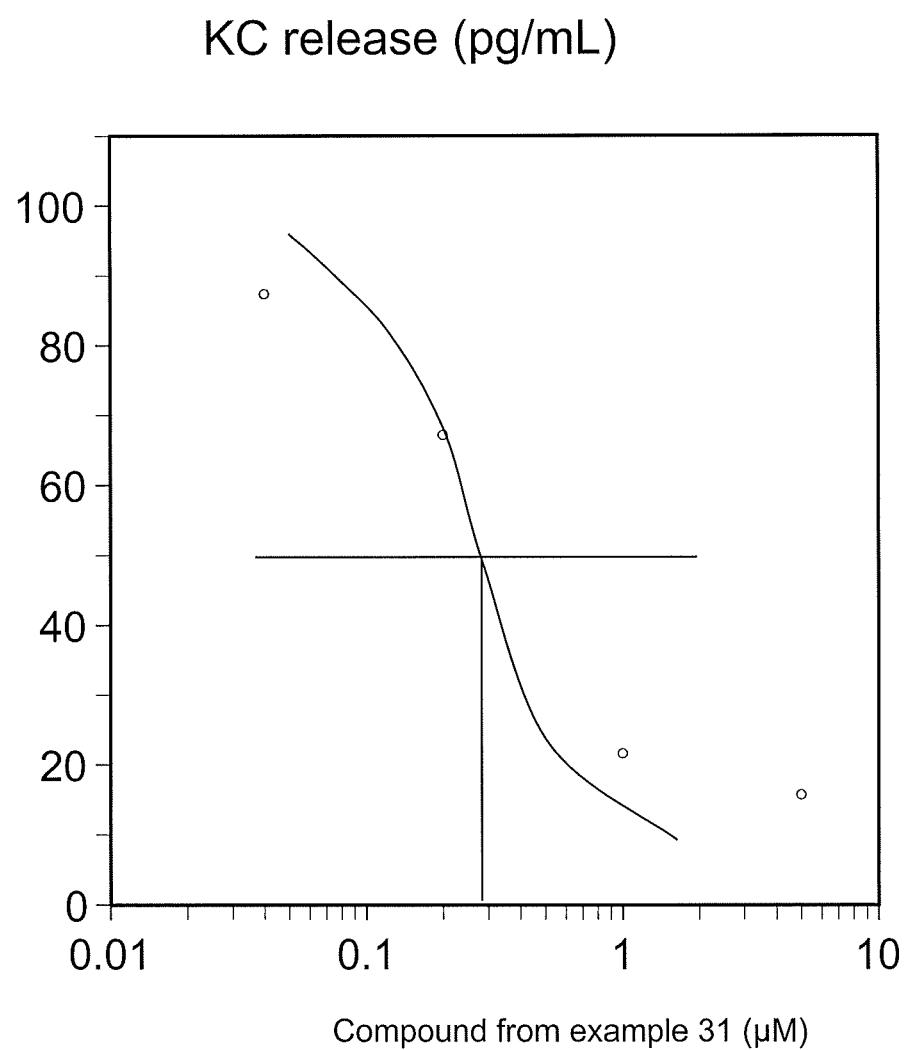
FIG. 2. is a graph showing the response of murine blood cells to varying concentrations of a compound of the invention (see Example 31) based on the production of the chemotactic cytokine "KC". Fresh mouse whole blood was stimulated by LPS and incubated for 90 minutes. KC was quantified by bioplex.

This invention relates to novel, semisynthetic macrocycles related to the erythromycine and azalide series, particularly to derivatives of erythromycin and azithromycin and to pharmaceutically acceptable addition salts thereof, to a process and intermediates for the preparation thereof, and to their use in the preparation of pharmaceuticals for the treatment of inflammations, neoplasms, metabolic diseases, cardiovascular diseases and infections.

According to the invention, it is possible to exploit a wide range of macrocycle structures for diverse pharmaceutical uses with reduced danger of promoting bacterial resistance to this drug class amongst the patient population.

It is well known that macrocyclic compounds present good physical and pharmaceutical properties, however, their antibacterial action restricts broader uses. However, due to their complex structure, further derivatization can be difficult, especially on large scale. To allow both reduction in antibacterial activity and facile, high yielding derivative formation, it would be desirable to find methods for preparation of reactive intermediates and facile purification methods.

Thus, according to the present invention, macrocycles may be conveniently modified at the secondary hydroxyl and amine on the desosamine ring.

The modifications can have at least three main effects:
Changes in physical properties
Reduction in antibiotic activity in some examples
Addition of sites for derivatisation to add functional groups including pharmacophores and heterocycles.

Exemplary modifications include but are not limited to: group transpositions, eliminations, reductive amination, mesylation, halogenation, tosylation, oxidation, alkylation, formation of epoxides, Amino derivatives, intra-lactone ring cyclisations, substitutions of hydroxyl groups for amine groups, removal of amines, addition of reactive sites (e.g. bromo, hydroxyl etc.), exchanges of sugars for cyclic or aliphatic groups, combinations of these modifications. The products and/or intermediates derived from these modifications can be further modified chemically via hydrolysis (including removal of cladinose), oxidation (includes formation of ketones), reductive amination, acylation, alkylation, nucleophilic substitution, rearrangements among others. On the intermediates prepared from these processes, pharmacophore or functionalized moieties can be attached. Without wishing to be bound by any particular theory, it is believed that the modifications change ring geometry, modifying activity and physical properties such as polarity, which in turn may alter permeation and formulation properties in addition to changes in the activity of the substance as an anti-biotic, anti-inflammatory, anti-proliferative and other activities. The resulting substances may also be conjugated with other active substances (such as drugs) so as to act as a prodrug. The invention also features a means of treating disease and formulations of these substances in pharmacologically acceptable vehicles.

The compounds so derived from macrocyclic starting points may serve as anti-inflammatory compounds, protease inhibitors, anti-viral compounds, anti-bacterial compounds, modulators of ion-channels, inhibitors of neurodegeneration, cardio-vascular modulators, metabolic modulators and immune modulators.

The invention allows the design of macrocycles that can be selectively modified to promote their activity as drug carriers and scaffolds for further derivatisation toward structures with direct drug-like activity without at the same time maintaining complete or partial (even less desirable) anti-biotic activity.

In the present invention this concept is elaborated using epoxide products from the erythromycin-derived macrocycles and the azalide class of macrocycles.

The invention features:
Formation of two types of epoxides on the desosamine ring of a macrolide and purifying the product by an upscalable process.
Further reaction of the epoxides with nucleophiles.
Substitution with low molecular weight groups with reactive sites.
Further derivatisation of the reactive groups with complex substituents.
These changes provide highly functionalized molecules that can be utilized according to user-specification (i.e. structurally diverse libraries of compounds, building blocks, pharmacophores, drug scaffolds, drug carriers, etc.)
3'-N-demethylamino derivatives of azithromycin, erythromycin or related macrolides, containing an oxiranyl, oxiranylalkyl or oxiranylaryl, or halogen-alkyl, halogenaryl, sulfonic ester, aminoaryl, aminoalkyl substituent to the 3'-amino function
Further reaction of these activated intermediates with small molecules containing one or several groups such as aldehyde, amino, hydrazino, azido, carboxy, hydroxy, boronates, cyano, and malono or malonate functions or bifunctional 1,3-carbonyl or carboxyl reagents.
Further derivatisation of these activated intermediates with complex molecules especially leading to ring formation or further bond formation, in particular, aromatic, heteroaromatic, heterocyclic ring systems with substitutions including bromo, fluoro, chloro, hydroxy, cyano, carbonyl, carboxamide, sulphonamide, amino, amido, mercapto, sulfonyl, sulfanyl.
Usage of functionalised intermediates to synthesise macrolide-substituted derivatives of known functional molecules including, but not limited to sterols, nuclear receptor ligands, kinase inhibitors, nucleosides, anti-inflammatory structures or protease inhibitors.

DEFINITIONS

Before further description of the present invention, and in order that the invention may be more readily understood, certain terms are first defined and collected here for convenience.

A "therapeutic agent," as used herein, is a molecule with pharmacological activity (e.g., a therapeutic agent, medicine, medicament, or active agent), a disease modification agent, or any other molecule or fragment of a therapeutic agent that can be covalently attached to a macrocycle via a bond or a linker which may have a desirable mode of action in target cells.

The term "cyclic" refers to a hydrocarbon cyclic ring including fully saturated, partially saturated, and unsaturated mono-, bi, and tri-cyclic rings having 4 to 34 ring atoms, preferably, 7 to 10, or 10 to 15 ring atoms. The term "heterocyclic" refers to a hydrocarbon cyclic ring including fully saturated, partially saturated, and unsaturated mono-, bi, and tri-cyclic rings having 4 to 34 ring atoms, preferably, 7 to 10, or 10 to 15 ring atoms having one or more heteroatoms, such as S, O, or N in each ring.

The term "sugar" refers to a mono-, di-, or tri-saccharide including deoxy-, thio-, and amino-saccharides. Examples of sugars include, but are not limited to, furanose and pyranose.

The terms "halogen" and "halo" refer to radicals of fluorine, chlorine, bromine or iodine.

The terms "macrolactone" or "macrocycle" are known in the art and refer to compounds having large lactone ring (i.e., cyclic ester) having at least 10 ring atoms. The term "macrolide" refers to a chemical compound characterized by a large lactone ring (having at least 10 ring atoms) containing one or more keto and hydroxyl groups, or to any of a large group of antibacterial antibiotics containing a large lactone ring linked glycosidically to one or more sugars; they are produced by certain species of *Streptomyces* and inhibit protein synthesis by binding to the 50S subunits of 70S ribosomes. Examples include erythromycin, azithromycin, and clarithromycin. The term "ketolide" refers to a chemical compound characterized by a large lactone ring (having at least 10 ring atoms) containing one or more keto groups.

The term "alkyl" (or "alkenyl" or "alkynyl") refers to a hydrocarbon chain that may be a straight chain or branched chain, containing the indicated number of carbon atoms. For example, $C_1$-$C_{10}$ indicates that the group may have from 1 to 10 (inclusive) carbon atoms in it. Alkenyl groups and alkynyl groups have one or more double or triple carboN-carbon bonds, respectively, in the chain.

The term "aryl" refers to a hydrocarbon ring system (monocyclic or bicyclic) having the indicated number of carbon atoms and at least one aromatic ring. Examples of aryl moieties include, but are not limited to, phenyl, naphthyl, and pyrenyl.

The term "heteroaryl" refers to a ring system (monocyclic or bicyclic) having the indicated number of ring atoms including carbon atoms and at least one aromatic ring. The ring system includes at least one heteroatom such as O, N, or S (e.g., between 1 and 4 heteroatoms, inclusive, per ring) as part of the ring system. Examples of heteroaryl moieties include, but are not limited to, pyridyl, furyl or furanyl, imidazolyl, benzimidazolyl, pyrimidinyl, thiophenyl or thienyl, quinolinyl, indolyl, and thiazolyl.

The term "alkoxy" refers to an —O-alkyl radical.

The term "cycloalkyl" refers to a nonaromatic hydrocarbon ring system (monocyclic or bicyclic), containing the indicated number of carbon atoms.

The term "heterocycloalkyl" refers to a nonaromatic ring system (monocyclic or bicyclic), containing the indicated number of ring atoms including carbon atoms and at least one heteroatom such as O, N, or S (e.g., between 1 and 4 heteroatoms, inclusive, per ring) as part of the ring system.

The term "effective amount" includes an amount effective, at dosages and for periods of time necessary, to achieve the desired result, e.g., sufficient to treat a cell proliferative disorder. An effective amount of compound of the invention may vary according to factors such as the disease state, age, and weight of the subject, and the ability of the compound of the invention to elicit a desired response in the subject. Dosage regimens may be adjusted to provide the optimum therapeutic response. An effective amount is also one in which any toxic or detrimental effects (e.g., side effects) of the compound of the invention are outweighed by the therapeutically beneficial effects.

The term "subject" includes organisms which are capable of suffering from a disease or disorder, e.g., as described herein (including an inflammatory, viral, bacterial, cardio-vascular modulators, metabolic or immune disorder), or who could otherwise benefit from the administration of a compound of the invention, such as human and non-human animals. Preferred humans include human patients suffering from or prone to suffering from a disease or disorder or associated state, as described herein (including an inflammatory, viral, bacterial, cardio-vascular modulators, metabolic or immune disorder). The term "non-human animals" of the invention includes all vertebrates, e.g., mammals, e.g., rodents, e.g., mice, and non-mammals, such as non-human primates, e.g., sheep, dog, cow, chickens, amphibians, reptiles, etc.

The compounds described herein have a range of utilities including use as anti-inflammatory compounds, protease inhibitors, inhibitors of neuro-degeneration, anti-viral compounds, anti-bacterial compounds, modulators of ion-channels, cardio-vascular modulators, metabolic modulators and immune modulators. In many instances, their utility may be related to effects on cells of the macrophage type either as phagocytes or antigen presenting cells. Such an example is seen in cardiovascular diseases such as atherosclerosis where there is a strong inflammatory component to the events that result in the thickening and fragmentation of the vessel obstructing plaques. This inflammation may be effectively reduced by the application of a range of agents that interact with the macrophage class.

The compounds described herein include the compounds themselves, as well as their salts, including pharmaceutically acceptable salts, if applicable. Such salts, for example, can be formed between a positively charged substituent (e.g., amino) on a compound and an anion. Suitable anions include, but are not limited to, chloride, bromide, iodide, sulfate, nitrate, phosphate, citrate, methanesulfonate, trifluoroacetate, and acetate. Likewise, a negatively charged substituent (e.g., carboxylate) on a compound can form a salt with a cation. Suitable cations include, but are not limited to, sodium ion, potassium ion, magnesium ion, calcium ion, and an ammonium cation such as tetramethylammonium ion.

In addition, some of the compounds of this invention have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms.

Further, the aforementioned compounds also include their N-oxides. The term "N-oxides" refers to one or more nitrogen atoms, when present in a compound, are in N-oxide form, i.e., N→O.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., treating a disease).

Process for Preparing and/or Purifying 2',3'-Epoxides of Macrocycles

As described herein, macrocycles may be conveniently modified at the amino function on the desosamine ring (position 3'). It has now been found that a good starting point for performing transformation chemistry on macrolide antibiotics and their derivatives is generating an epoxide on the desosamine ring. One example of an epoxidation reaction is described in PCT03/070174 (Burnet et al) and PCT03/070173 (Burnet et al) where a laboratory scale process is reported. Although adequate for discovery purposes, this process was not optimal for large scale chemistry. The process described herein provides for superior yields and purity in larger scale.

In PCT03/070174 (Burnet et al) and PCT03/070173 (Burnet et al) it has been already disclosed that treating a solution of azithromycin in DMF with an excess of epichlorohydrin at temperatures between 60 and 120° C. yields a less polar product. This product was identified to be an epoxide (the 2',3' desosamine epoxide, see, e.g., Example 1). Without wishing to be bound by theory, the reaction mechanism may involve the alkylation of the dimethyl amino group followed by displacement with the 2'-hydroxyl group. In these earlier references, purification of the product was then usually carried out by chromatography on silica gel.

The present inventors have now discovered a straightforward, up-scalable process for performing the elimination/epoxide-formation reaction and purifying of the reaction product.

Thus, in one aspect, the present invention provides a method for purifying a 2',3'-epoxy macrolide (preferably an azalide). The method includes the steps of: a) providing the 2',3'-epoxy macrolide; b) contacting the 2',3'-epoxy macrolide with an aqueous solvent and a base under conditions such that the 2',3'-epoxy macrolide precipitates; and c) collecting the precipitated 2',3'-epoxy macrolide. In preferred embodiments, the macrolide is an azalide, even more preferably a derivative of azithromycin. In preferred embodiments, the step of providing the macrolide comprises preparing the macrolide, e.g., by reacting a macrolide with an alkylating reagent such as epichlorohydrin, such that the 2',3'-epoxy macrolide is prepared. The reaction may occur in a solvent, such as DMF. The step of contacting can include adding the 2',3'-epoxy macrolide (preferably after removing at least some of the solvent from the reacting step) to a solvent mixture which includes at least some water (e.g., 20%, 40%, 60% or 80% water) preferably mixed with a water-miscible organic solvent.

The process involves carrying out the epoxidation/elimination reaction and then removing most of the excess reagents (such as epichlorohydrin) and the DMF by transferring the viscous residue into a stirred vessel containing water with a certain content of a water miscible solvent (e.g., isopropanol, acetone, methyl or ethyl alcohol) and a base (e.g., an inorganic base like alkali hydroxides (such as sodium, potassium, or lithium hydroxides) or carbonates (such as sodium, potassium, or lithium carbonates). Frequently, precipitation of the epoxide product will take place that can be assisted with seeding and/or ultrasonication. Collection of the product by filtration after some period to allow further precipitation will yield a crude product that can be easily purified, e.g., by crystallisation, e.g., from hot isopropanol. Concentration of the mother liquor may yield a second crop of solid that can be similarly purified by recrystallisation from isopropanol. Yields are typically between 30 and 55%. Advantageously, no chromatographic purification is necessary.

In certain preferred embodiments: epichlohydrin is used to cause elimination of the 3-dimethylamino moiety of the macrolide and epoxide formation; the epoxide product is isolated from the reaction mixture using a water miscible organic solvent; the water miscible organic solvent is an alcohol; the water miscible organic solvent is used at a temperature of 0 to 15 C; the crude 2',3'-epoxide product is recrystallised from an organic solvent, more preferably isopropanol.

Production of Olefinic Compounds by Cope Elimination

The present inventors have discovered that it is also possible to generate a previously-unknown different epoxide (the 3',4'-epoxide) on the desosamine sugar of azalides. Thus, the present invention provides novel epoxide-containing compounds and methods for their preparation and use.

In general, the methods of synthesis of the new compounds features generation of a tertiary amine oxide on the 3-dimethylamino moiety of the aminosugar portion of the macrolide. This can be achieved by treating an azalide macrolide, for example azithromycin with an oxidising agent (e.g., hydrogen peroxide or a peracid like acetic peracid or 3-chloroperbenzoic acid (MCBPA)). Heating of such an amine oxide can lead to formation of an olefinic double bond by elimination of a hydroxylamine. This reaction is known as the Cope Elimination and typically occurs with heating of the amine oxide compound, e.g., to between 80 and 160° C.

In general, the reaction requires heating to a temperature of 130-230° C., preferably a temperature between 150-170° C. The compound can be heated, e.g., under vacuum in a glass oven (Kugelrohr apparatus). The reaction can be performed in an inert reaction medium like a high boiling hydrocarbon like xylene, mesytylene or paraffin oil, but more preferably is performed neat (without solvent) while applying a vacuum of 0.1-30 mbar. Under these conditions a product such as the olefin derived from azithromycin may be formed as a honey-like liquid at high temperature and a glass like solid upon cooling. Purification can be achieved simply by taking up the reaction product in an organic solvent like ethyl acetate or acetonitrile and filtration of the solution through a pad of silica gel and elution with the same solvent. Evaporation of the solvent can yield a solid that is pure enough for most reactions and can be further purified by recrystallisation, e.g., from acetonitrile.

The product obtained by this procedure is a versatile starting point for many transformations, including but not limited to epoxidation, bishydroxylation, aminohydroxylation, reduction, oxidation, palladium catalyzed acrylic or vinylic coupling and others. Products obtained by any of these transformations may be further derivatised by reaction typed cited above or other ones, for example nucleophilic reaction of an amine or an organometallic nucleophile on an epoxide. One of many possible transformations is the epoxidation of the product obtained from the Cope elimination step. Opening the epoxide with dimethylamine under appropriate conditions will result after reduction of generally formed tertiary amine oxide during the epoxidation reaction in the formation of the sugar mycaminose instead of desosamine in the parent compound of azithromycin.

The invention thus provides certain 3',4'-olefinic macrolide compounds. In one aspect, the invention provides a compound which is a 3',4'-olefinic macrolide. In one embodiment, the invention provides a compound represented by the formula (Formula I):

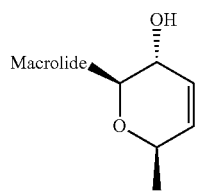

in which Macrolide is a macrocylic macrolide moiety selected from the group consisting of macrolides, macrolactones and azalides. In a preferred embodiment, the macrolide is the macrocyclic ring of azithromycin (together with the associated cladinose sugar). The invention also provides pharmaceutically acceptable salts of compounds of Formula I.

In another aspect, the invention provides a method of making a 3',4'-olefinic macrolide, e.g., a compound of Formula I, the method comprising heating a 3-N',N'-dialkyl-amino N' oxide (preferably N,N-dimethylamino) macrolide compound under conditions such that a 3',4'-olefinic azalide is formed. In a preferred embodiment, the macrolide is the macrocyclic ring of azithromycin (together with the associated cladinose sugar). The method optionally includes the step of isolating or purifying the compound of Formula I.

Production of 3',4'-Epoxy Macrolide Compounds by Cope Elimination

The 3',4' double bond of a 3',4'-olefinic macrolide compound of the invention (e.g., a compound of Formula I, e.g., a compound produced by the methods described herein), can be subjected to conditions that will result in epoxide formation on the desosamine. A typical reagent to achieve this transformation is an oxidizing reagent such as 3-chloroperbenzoic acid (MCBPA). Under these conditions, any remaining tertiary amine of the macrolide (e.g., N–1 of the macrolide) may also react and be converted to an amine oxide. See, e.g., Compound B of FIG. 1 for an example of such a chemical structure.

In one aspect, the invention provides a 3',4'-epoxy macrolide compound, e.g., a compound represented by the formula (Formula II):

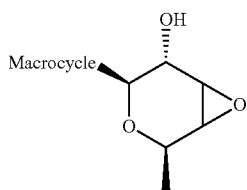

in which Macrolide is a macrolide moiety selected from the group consisting of macrolides, macrolactones and azalides. In a preferred embodiment, the macrolide is the macrocyclic ring of azithromycin (together with the associated cladinose sugar). The invention also provides pharmaceutically acceptable salts of compounds of Formula II.

In a preferred embodiment, the 3',4'-epoxy macrolide compound is represented by the structure:

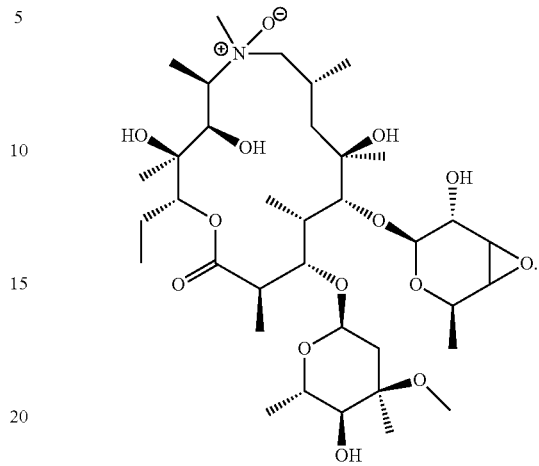

In another aspect, the invention provides a method of making a 3',4'-epoxy macrolide compound of Formula II. The method includes the steps of: a) treating a compound of Formula II with an epoxidizing reagent under conditions such that the compound of Formula II is prepared. The method optionally includes the step of isolating or purifying the compound of Formula II.

Elaboration of Epoxides to Yield Pharmacologically-Active Molecules

Chemical structures such as the epoxymacrolides of the invention (e.g., Compound A of FIG. 1) are well suited for chemical derivatisation due to the reactive epoxide moiety. Combining Compound A with different nucleophiles can generate a multitude of compounds. Because the macrocycle backbone provides for good solubility and membrane permeability, these products do not generally suffer from the typical disadvantages typically encountered while constructing simple chemical libraries like poor physico-chemical properties and low water solubility. Indeed, the large macrocycle can confer superior properties, such as oral availability, cellular penetration, intracellular accumulation, and the like.

Elaboration of the epoxide-containing compounds of the invention (e.g., 2',3'-epoxides such as Compound A and 3,4-epoxides such as Compound B of FIG. 1) can be carried out with inorganic or organic salts like alkali azides, cyanides, acetates, thiocyanates, neutral nucleophiles like aliphatic, aromatic, heteroaromatic amines or heterocycles containing an amine like imidazole. Substituted or unsubstituted hydrazines can be used. Also salts like hydrochlorides of such nucleophiles can be employed, e.g. hydroxylamine hydrochloride. Another class of compounds is represented by carbon nucleophiles including esters of malonic acid. It has to be noted that a nucleophilic molecule or moiety can attack the epoxide principally on two sites, generally yielding a mixture of products, thus increasing the scope of the reaction and the variability of the products. It has also to be noted that a moiety entering the epoxide-macrolide at the 2'-position will give rise to a compound with a different regiochemistry than for example azithromycin. A dramatic decrease of antibacterial activity is possible in such a case.

Advantageously, derivatization may take place through either a mono or an oligofunctional molecule so that further chemistry in one or several following steps may take place. For example, substitution with ammonia will generate a primary amine which can be subjected to alkylation (e.g., reductive alkylation with aldehydes, or nucleophilic alkylation with, e.g., an alkyl halide, see, e.g., the Examples herein). Reaction of the epoxide moiety with a diamine like piperazine offers another reaction site for subsequent alkylation or acylation reactions. Alkylations may for example be performed with dibromopropane. In this case, an additional electrophilic site ready for further displacement is provided; for example, a bromide may react with hydrazine which in turn will react to form pyrazole derivatives on exposure to 1,3-dicarbonyl/carboxyl derivatives.

Complex structures can be built on macrolides such as Compounds A or B (FIG. 1). These structures may include pharmacophores for a variety of molecular targets within or outside of a cell. In one aspect, the macrocyclic backbones provide a means for the functionalized molecules to enter the cells; in another aspect, the macrocycle stabilizes the molecule or makes it easier to prepare, formulate or manufacture.

Another aspect of the invention is that further variation is possible especially when the entering group has a basic nature thus making the sugar moiety more resistant towards acidic hydrolysis. For example, acidic hydrolysis will then result in removal of the cladinose sugar. It is well established that such a modification will greatly diminish the antibiotic potential of a macrolide of this class.

Exemplary compounds, e.g., compounds that can be prepared using the epoxy or olefinic macrolide compounds of the invention, are described infra.

Derivatives of N-des-methyl Desosamine Containing Macrocycles

It is known that erythromycin can be easily demethylated at the amino function in the 3'-position on the desosamino sugar. This reaction can also be applied to other macrolide derivatives like azithromycin or 2-ethyl-3,4,10-trihydroxy-11-[3-hydroxy-6-methyl-4-(methyl-oxiranylmethyl-amino)-tetrahydro-pyran-2-yloxy]-3,5,6,8,10,12,14-heptamethyl-1-oxa-6-aza-cyclopentadecane-13,15-dione. During examination of the formation of 3'-dedimethylamino-2'-dehydroxy-2',3'-epoxyazithromycin it was surprisingly found, that the desamination does not occur on the demethylated derivative of azithromycin, but smoothly leads to the introduction of an oxiranylmethyl side chain to the nitrogen. This reaction can be applied to other 3'-N-demethylmacrolides, too. Other alkylating agents are also insufficient for desamination, but lead only to monoalkylation of the nitrogen in position 3'. In certain embodiments, the reaction is carried out in concentrated solution in 2-propanol with an excess of epichlorohydrin in the presence of potassium carbonate at room temperature. It usually gives excellent yields; purification can be achieved by recrystallisation.

Exemplary compounds, e.g., compounds that can be prepared from N-desmethyl desosamine-containing macrocycles, are described infra.

Elaboration of Activated Forms of N-Desmethyl Macrolides

The present invention also relates to the synthesis of different activated intermediates that are suitable for further easy derivatisation steps on the desosamine side chain of azithromycin, and the use of these compounds for the above mentioned purpose. This includes the opening of the epoxide rings with any type of nucleophiles, for example, but not limited to amines, carboxylates, phenols, sulfides, inorganic nucleophiles like hydroxylamines, hydrazines, cyanides, azides or thiocyanates or C-nucleophiles like malonates or acetoacetates, or substitution of alkylhalogenides or other alkylating functions with these nucleophiles. In certain embodiments, this chemistry is similar to the chemistries used for elaboration of 2',3'-epoxy compounds such as Compound A, e.g., as described supra.

The compounds thus formed may be pharmacologically active themselves or may be starting points for the synthesis of more complex structures; accordingly, the invention includes compounds which incorporate structural elements of known activity, like, for example, kinase inhibiting cores or kinase inhibitors or protease inhibitors, linked to the macrolide core for improvement of their properties, as well as methods of preparing and using such compounds. Improvement in properties is intended to include (but is not limited to) improvements in their physical properties, their toxicity, taste, specific activating or inhibiting activity, distribution pattern in an organism or improved retention or excretion from a body, in comparison to the underivatized active compounds.

Compounds

Thus, in one aspect, the invention provides novel compounds. In one embodiment, the invention provides compounds represented by the formula (Formula III):

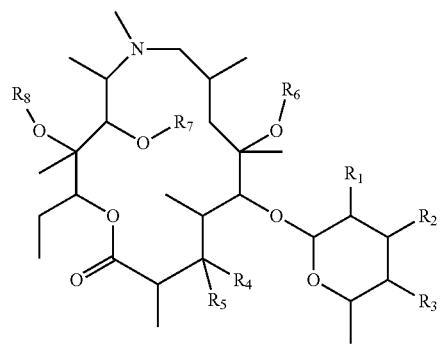

wherein:

$R^1$=OH, O-acyl, $N_3$, $NH_2NH_2$, $NR_2$ (in which both R residues can independently mean: H, alkyl, aryl, heteroaryl);

$R^2$=OH, O-acyl, $NR_2$ (in which both R residues can independently mean: H, alkyl, aryl, heteroaryl);

or $R^1$ and $R^2$ may independently represent more complex residues, for example mono- or oligofunctional moieties (polyamines, bicyclic systems, peptides amines, halogenides, sulphonic esters, acetals, esters, aldehydes, sulfones, sulfonamides, lactones, boronates, silicates, hydroxylamines, alcohols or any type of heterocycle such as imidazoles, thiazoles pyrimidines and combinations thereof), pharmacophores (e.g. sterols, hormones, peptide analogs, nucleosides, anti-inflammatory structures, protease inhibitors, kinase inhibitors) or specifically reactive functions (hydrazines, amino groups, 1,3-dicarbonyl or carboxyl groups, bromoalkyl and bromoaryl groups) that may be conveniently reacted with reagents to form heterocyclic residues or cyclic or heterocyclic assemblies);

$R^3$=H, OH, O-alkyl, O-acyl $R^4$=H $R^5$=cladinosyl, OH, or $R^4$, $R^5$ is =O $R^6$=H, methyl, $R^7$, $R^8$=H, acyl, or $R^7$, $R^8$=CO (cyclic carbonate);

with the proviso that the compound is not azithromycin; or a pharmaceutically acceptable salt thereof.

In one embodiment, the invention provides compounds represented by the formula (Formula IV):

in which
$R^1$, $R^2$=independently H, alkyl (e.g., $C_1$-$C_{10}$ alkyl), aryl, or heteroaryl; or $R^1$ and $R^2$ may independently represent more complex residues, for example mono- or oligofunctional moieties (polyamines, bicyclic systems, peptides amines, halogenides, sulphonic esters, acetals, esters, aldehydes, sulfones, sulfonamides, lactones, boronates, silicates, hydroxylamines, alcohols or any type of heterocycle such as imidazoles, thiazoles pyrimidines and combinations thereof), pharmacophores (e.g. sterols, hormones, peptide analogs, nucleosides, anti-inflammatory structures, protease inhibitors, kinase inhibitors) or specifically reactive functions (hydrazines, amino groups, 1,3-dicarbonyl or carboxyl groups, bromoalkyl and bromoaryl groups) that may be conveniently reacted with reagents to form heterocyclic residues or cyclic or heterocyclic assemblies);
$R^3$=OH, O-acyl
$R^4$=H
$R^5$=cladinosyl, OH, or $R^4$, $R^5$ is =O
$R^6$=H, methyl,
$R^7$, $R^8$=H, acyl, or $R^7$, $R^8$=CO (cyclic carbonate); or a pharmaceutically acceptable salt thereof.

In certain preferred embodiments, the invention provides compounds represented by the formula (Formula V):

wherein:
$R^1$, $R^2$=independently H, alkyl (e.g., $C_1$-$C_{10}$ alkyl), aryl, or heteroaryl; or $R^1$ and $R^2$ may independently represent more complex residues, for example mono- or oligofunctional moieties (polyamines, bicyclic systems, peptides amines, halogenides, sulphonic esters, acetals, esters, aldehydes, sulfones, sulfonamides, lactones, boronates, silicates, hydroxylamines, alcohols or any type of heterocycle such as imidazoles, thiazoles pyrimidines and combinations thereof), pharmacophores (e.g. sterols, hormones, peptide analogs, nucleosides, anti-inflammatory structures, protease inhibitors, kinase inhibitors) or specifically reactive functions (hydrazines, amino groups, 1,3-dicarbonyl or carboxyl groups, bromoalkyl and bromoaryl groups) that may be conveniently reacted with reagents to form heterocyclic residues or cyclic or heterocyclic assemblies);
$R^3$=H, acyl, alkyl
$R^4$=H
$R^5$=cladinosyl, OH, or $R^4$, $R^5$ is =O
$R^6$=H, methyl,
$R^7$, $R^8$=H, acyl, or $R^7$, $R^8$=CO (cyclic carbonate); or a pharmaceutically acceptable salt thereof.

In certain preferred embodiment, the invention provides compounds represented by the formula (Formula VI):

wherein:
$R^1$, $R^2$=independently H, alkyl (e.g., $C_1$-$C_{10}$ alkyl), aryl, or heteroaryl; or $R^1$ and $R^2$ may independently represent more complex residues, for example mono- or oligofunctional moieties (polyamines, bicyclic systems, peptides amines, halogenides, sulphonic esters, acetals, esters, aldehydes, sulfones, sulfonamides, lactones, boronates, silicates, hydroxylamines, alcohols or any type of heterocycle such as imidazoles, thiazoles pyrimidines and combinations thereof), pharmacophores (e.g. sterols, hormones, peptide analogs, nucleosides, anti-inflammatory structures, protease inhibitors, kinase inhibitors) or specifically reactive functions (hydrazines, amino groups, 1,3-dicarbonyl or carboxyl groups, bromoalkyl and bromoaryl groups) that may be conveniently reacted with reagents to form heterocyclic residues or cyclic or heterocyclic assemblies); or $R_1$ and $R_2$, taken together with the nitrogen atom to which they are attached, form a carbocyclic or heterocyclic ring having one to ten atoms in the ring;
$R^3$=H, acyl, alkyl
$R^4$=H
$R^5$=cladinosyl, OH, or $R^4$, $R^5$ is =O
$R^6$=H, methyl,
$R^7$, $R^8$=H, acyl, or $R^7$, $R^8$=CO (cyclic carbonate); or a pharmaceutically acceptable salt thereof.

In another embodiment, the invention provides compounds represented by the formula (Formula VII):

wherein:

R[1], R[2]=independently H, alkyl (e.g., $C_1$-$C_{10}$ alkyl), aryl, or heteroaryl; or R[1] and R[2] may independently represent more complex residues, for example mono- or oligofunctional moieties (polyamines, bicyclic systems, peptides amines, halogenides, sulphonic esters, acetals, esters, aldehydes, sulfones, sulfonamides, lactones, boronates, silicates, hydroxylamines, alcohols or any type of heterocycle such as imidazoles, thiazoles pyrimidines and combinations thereof), pharmacophores (e.g. sterols, hormones, peptide analogs, nucleosides, anti-inflammatory structures, protease inhibitors, kinase inhibitors) or specifically reactive functions (hydrazines, amino groups, 1,3-dicarbonyl or carboxyl groups, bromoalkyl and bromoaryl groups) that may be conveniently reacted with reagents to form heterocyclic residues or cyclic or heterocyclic assemblies); or $R_1$ and $R_2$, taken together with the nitrogen atom to which they are attached, form a carbocyclic or heterocyclic ring having one to ten atoms in the ring;

R[3]=H, acyl, alkyl

R[4]=H

R[5]=cladinosyl, OH, or R[4], R[5] is =O

R[6]=H, methyl,

R[7], R[8]=H, acyl, or R[7], R[8]=CO (cyclic carbonate); or a pharmaceutically acceptable salt thereof.

However, in preferred embodiments, the compound is not:

In another embodiment, the invention provides compounds represented by the formula (Formula VIII):

wherein:

R[1]=H, lower alkyl

R[2]=H, OH, O-alkyl, $NH_2$, $NH_2NH_2$, halogen, SH, aryl, heteroaryl, or a combination of several of these elements.

R[3]=H, acyl, alkyl

R[4]=H

R[5]=cladinosyl, OH, or R[4], R[5] is =O

R[6]=H, methyl,

R[7], R[8]=H, acyl, or R[7], R[8]=CO (cyclic carbonate); or a pharmaceutically acceptable salt thereof.

In another embodiment, the invention provides compounds represented by the formula (Formula IX):

wherein:

R[1]=H, lower alkyl

R[2]=H, OH, O-alkyl, $NH_2$, $NH_2NH_2$, halogen, SH, aryl, heteroaryl, or a combination of several of these elements.

R[3]=H, acyl, alkyl

R[4]=H

R[5]=cladinosyl, OH, or R[4], R[5] is =O

R[6]=H, methyl,

R[7], R[8]=H, acyl, or R[7], R[8]=CO (cyclic carbonate); or a pharmaceutically acceptable salt thereof.

In another embodiment, the invention provides compounds represented by the formula (Formula X):

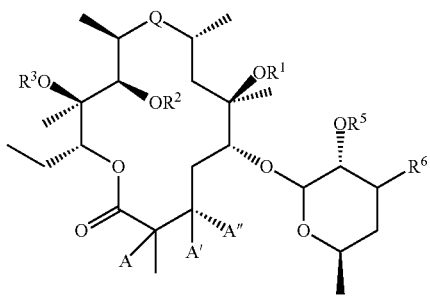

wherein

A, A' are Hydrogen or radicals forming a double bond and A" is H or OH or O-Cladinosyl;

or A=Hydrogen and A' and A" are double bound oxygen;

$R^1$-$R^3$, and $R^5$ are independently H, alkyl, acyl, allyl, vinyl, $SiR_3$ (R in this context may be alkyl or a combination of alkyl and aryl)

$R^2$, $R^3$ may be C=O (cyclic carbonate);

$R^6$=H, OH, CN, $N_3$, $NR^8{}_2$ ($R^8$ in this context may be H or alkyl or cycloalkyl), alkyl, cycloalkyl, —N(CH$_3$)$R^8$ ($R^8$ in this context may be H, alkyl, aryl, heteroaryl; it will be understood by the skilled artisan that more complex residues may be represented by this position, for example mono- or oligofunctional moieties or even pharmacophores or otherwise a desired activity causing assembly of chemical building blocks), or $SR^9$ ($R^9$ in this context may be H or alkyl or cycloalkyl);

Q=—(C=O)— or —(C=NY)— or —N(CH$_3$)—CH$_2$— or —N(Y)—CH$_2$—, or —CH$_2$—N(Y)— where Y=H, alkyl, aryl, heteroalkyl, heteroaryl, allyl or alkylheteroaryl or O-Alkyl or O-aryl;

or a pharmaceutically acceptable salt thereof.

In another embodiment, the invention provides compounds represented by the formula (Formula XI):

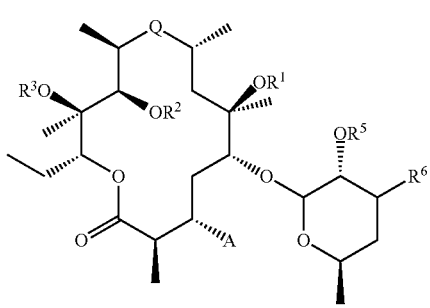

wherein

A =OH or O-cladinosyl $R^1$-$R^3$, and $R^5$ are independently H, alkyl, acyl, allyl, vinyl, $SiR_3$ (R in this context may be alkyl or a combination of alkyl and aryl)

$R^2$, $R^3$ may be C=O (cyclic carbonate)

$R^6$=independently H, alkyl (e.g., $C_1$-$C_{10}$ alkyl), aryl, or heteroaryl; or $R^1$ and $R^2$ may independently represent more complex residues, for example mono- or oligofunctional moieties (polyamines, bicyclic systems, peptides amines, halogenides, sulphonic esters, acetals, esters, aldehydes, sulfones, sulfonamides, lactones, boronates, silicates, hydroxylamines, alcohols or any type of heterocycle such as imidazoles, thiazoles pyrimidines and combinations thereof), pharmacophores (e.g. sterols, hormones, peptide analogs, nucleosides, anti-inflammatory structures, protease inhibitors, kinase inhibitors) or specifically reactive functions (hydrazines, amino groups, 1,3-dicarbonyl or carboxyl groups, bromoalkyl and bromoaryl groups) that may be conveniently reacted with reagents to form heterocyclic residues or cyclic or heterocyclic assemblies);

Q=—(C=O)— or —(C=NY)— or —N(CH$_3$)—CH$_2$— or —N(Y)—CH$_2$—, or —CH$_2$—N(Y)— where Y=H, alkyl, aryl, heteroalkyl, heteroaryl, allyl or alkylheteroaryl or O-Alkyl or O-aryl; or a pharmaceutically acceptable salt thereof.

In another embodiment, the invention provides compounds represented by the formula (Formula XII):

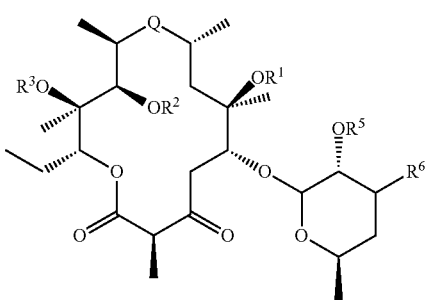

wherein $R^1$-$R^3$, and $R^5$ are independently H, alkyl, acyl, allyl, vinyl, $SiR_3$ (R in this context may be alkyl or a combination of alkyl and aryl)

$R^2$, $R^3$ may be C=O (cyclic carbonate)

$R^6$=independently H, alkyl (e.g., $C_1$-$C_{10}$ alkyl), aryl, or heteroaryl; or $R^1$ and $R^2$ may independently represent more complex residues, for example mono- or oligofunctional moieties (polyamines, bicyclic systems, peptides amines, halogenides, sulphonic esters, acetals, esters, aldehydes, sulfones, sulfonamides, lactones, boronates, silicates, hydroxylamines, alcohols or any type of heterocycle such as imidazoles, thiazoles pyrimidines and combinations thereof), pharmacophores (e.g. sterols, hormones, peptide analogs, nucleosides, anti-inflammatory structures, protease inhibitors, kinase inhibitors) or specifically reactive functions (hydrazines, amino groups, 1,3-dicarbonyl or carboxyl groups, bromoalkyl and bromoaryl groups) that may be conveniently reacted with reagents to form heterocyclic residues or cyclic or heterocyclic assemblies);

Q=—(C=O)— or —(C=NY)— or —N(CH$_3$)—CH$_2$— or —N(Y)—CH$_2$—, or —CH$_2$—N(Y)— where Y=H, alkyl, aryl, heteroalkyl, heteroaryl, allyl or alkylheteroaryl or O-Alkyl or O-aryl;

or a pharmaceutically acceptable salt thereof.

In another embodiment, the invention provides compounds represented by the formula (Formula XIII)

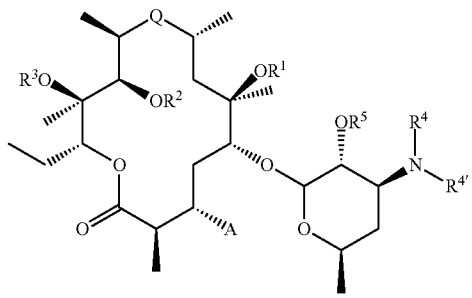

wherein
A =OH or O-cladinosyl
$R^1$-$R^3$, and $R^5$ are independently H, alkyl, acyl, allyl, vinyl, $SiR_3$ (R in this context may be alkyl or a combination of alkyl and aryl)
$R^2$, $R^3$ may be C=O (cyclic carbonate)
$R^4$ and $R^{4'}$ may be independently H, alkyl, heteroalkyl, cycloalkyl, heterocycloalkyl, vinyl, allyl, acyl, aryl, heteroaryl, alkylaryl, alkylheteroaryl; or independently H, alkyl (e.g., $C_1$-$C_{10}$ alkyl), aryl, or heteroaryl; or $R^4$ and $R^{4'}$ may independently represent more complex residues, for example mono- or oligofunctional moieties (polyamines, bicyclic systems, peptides amines, halogenides, sulphonic esters, acetals, esters, aldehydes, sulfones, sulfonamides, lactones, boronates, silicates, hydroxylamines, alcohols or any type of heterocycle such as imidazoles, thiazoles pyrimidines and combinations thereof), pharmacophores (e.g. sterols, hormones, peptide analogs, nucleosides, anti-inflammatory structures, protease inhibitors, kinase inhibitors) or specifically reactive functions (hydrazines, amino groups, 1,3-dicarbonyl or carboxyl groups, bromoalkyl and bromoaryl groups) that may be conveniently reacted with reagents to form heterocyclic residues or cyclic or heterocyclic assemblies);
Q=—(C=O)— or —(C=NY)— or —N($CH_3$)—$CH_2$— or —N(Y)—$CH_2$—, or —$CH_2$—N(Y)— where Y=H, alkyl, aryl, heteroalkyl, heteroaryl, allyl or alkylheteroaryl or O-Alkyl or O-aryl;
or a pharmaceutically acceptable salt thereof.

In another embodiment, the invention provides compounds represented by the formula (Formula XIV):

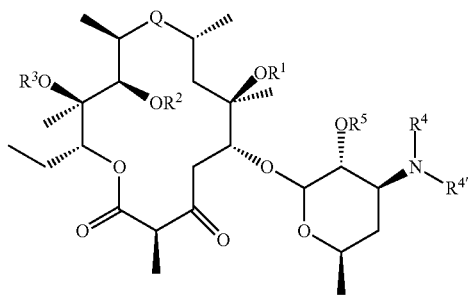

wherein
$R^1$-$R^3$, and $R^5$ are independently H, alkyl, acyl, allyl, vinyl, $SiR_3$ (R in this context may be alkyl or a combination of alkyl and aryl)
$R^2$, $R^3$ may be C=O (cyclic carbonate)
$R^4$ and $R^{4'}$ may be independently H, alkyl, heteroalkyl, cycloalkyl, heterocycloalkyl, vinyl, allyl, acyl, aryl, heteroaryl, alkylaryl, alkylheteroaryl; or $R^4$ and $R^{4'}$ may independently represent more complex residues, for example mono- or oligofunctional moieties (polyamines, bicyclic systems, peptides amines, halogenides, sulphonic esters, acetals, esters, aldehydes, sulfones, sulfonamides, lactones, boronates, silicates, hydroxylamines, alcohols or any type of heterocycle such as imidazoles, thiazoles pyrimidines and combinations thereof), pharmacophores (e.g. sterols, hormones, peptide analogs, nucleosides, anti-inflammatory structures, protease inhibitors, kinase inhibitors) or specifically reactive functions (hydrazines, amino groups, 1,3-dicarbonyl or carboxyl groups, bromoalkyl and bromoaryl groups) that may be conveniently reacted with reagents to form heterocyclic residues or cyclic or heterocyclic assemblies);
Q=—(C=O)— or —(C=NY)— or —N($CH_3$)—$CH_2$— or —N(Y)—$CH_2$—, or —$CH_2$—N(Y)— where Y=H, alkyl, aryl, heteroalkyl, heteroaryl, allyl or alkylheteroaryl or O-Alkyl or D-aryl;
or a pharmaceutically acceptable salt thereof.

In another embodiment, the invention provides compounds represented by the formula (Formula XV):

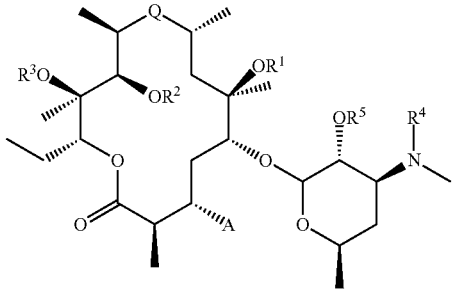

wherein
A =OH or O-cladinosyl
$R^1$-$R^3$, and $R^5$ are independently H, alkyl, acyl, allyl, vinyl, $SiR_3$ (R in this context may be alkyl or a combination of alkyl and aryl)
$R^2$, $R^3$ may be C=O (cyclic carbonate)
$R^4$ may be H, alkyl, heteroalkyl, cycloalkyl, heterocycloalkyl, vinyl, allyl, acyl, aryl, heteroaryl, alkylaryl, alkylheteroaryl; or $R^4$ may also represent more complex residues, for example mono- or oligofunctional moieties (polyamines, bicyclic systems, peptides amines, halogenides, sulphonic esters, acetals, esters, aldehydes, sulfones, sulfonamides, lactones, boronates, silicates, hydroxylamines, alcohols or any type of heterocycle such as imidazoles, thiazoles pyrimidines and combinations thereof), pharmacophores (e.g. sterols, hormones, peptide analogs, nucleosides, anti-inflammatory structures, protease inhibitors, kinase inhibitors) or specifically reactive functions (hydrazines, amino groups, 1,3-dicarbonyl or carboxyl groups, bromoalkyl and bromoaryl groups) that may be conveniently reacted with reagents to form heterocyclic residues or cyclic or heterocyclic assemblies);
Q=—(C=O)— or —(C=NY)— or —N($CH_3$)—$CH_2$— or —N(Y)—$CH_2$—, or —$CH_2$—N(Y)— where Y=H, alkyl, aryl, heteroalkyl, heteroaryl, allyl or alkylheteroaryl or O-Alkyl or D-aryl;
or a pharmaceutically acceptable salt thereof.

In another embodiment, the invention provides compounds represented by the formula (Formula XVI):

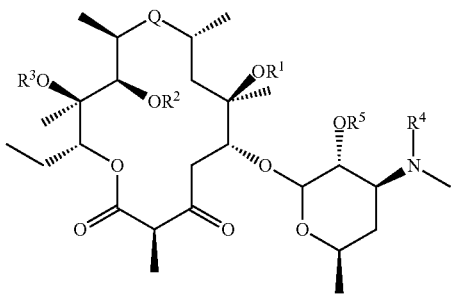

wherein
$R^1$-$R^3$, and $R^5$ are independently H, alkyl, acyl, allyl, vinyl, $SiR_3$ (R in this context may be alkyl or a combination of alkyl and aryl)

$R^2$, $R^3$ may be C=O (cyclic carbonate)

$R^4$ and $R^{4'}$ may be independently H, alkyl, heteroalkyl, cycloalkyl, heterocycloalkyl, vinyl, allyl, acyl, aryl, heteroaryl, alkylaryl, alkylheteroaryl; or $R^4$ and $R^{4'}$ may independently be H, alkyl, heteroalkyl, cycloalkyl, heterocycloalkyl, vinyl, allyl, acyl, aryl, heteroaryl, alkylaryl, alkylheteroaryl; or $R^4$ may also represent more complex residues, for example mono- or oligofunctional moieties (polyamines, bicyclic systems, peptides amines, halogenides, sulphonic esters, acetals, esters, aldehydes, sulfones, sulfonamides, lactones, boronates, silicates, hydroxylamines, alcohols or any type of heterocycle such as imidazoles, thiazoles pyrimidines and combinations thereof), pharmacophores (e.g. sterols, hormones, peptide analogs, nucleosides, anti-inflammatory structures, protease inhibitors, kinase inhibitors) or specifically reactive functions (hydrazines, amino groups, 1,3-dicarbonyl or carboxyl groups, bromoalkyl and bromoaryl groups) that may be conveniently reacted with reagents to form heterocyclic residues or cyclic or heterocyclic assemblies);

Q=—(C=O)— or —(C=NY)— or —N($CH_3$)—$CH_2$— or —N(Y)—$CH_2$—, or —$CH_2$—N(Y)— where Y=H, alkyl, aryl, heteroalkyl, heteroaryl, allyl or alkylheteroaryl or O-Alkyl or O-aryl;

or a pharmaceutically acceptable salt thereof.

In another embodiment, the invention provides compounds represented by the formula (Formula XVII):

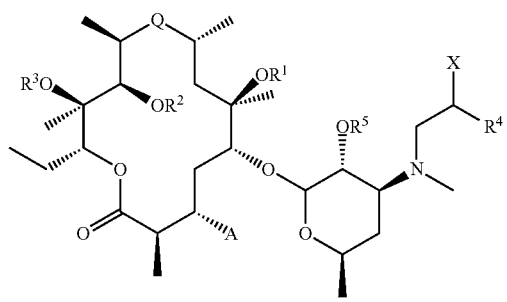

wherein
A =OH or O-cladinosyl
X=H or OH or NH(R). R in this context means H, lower alkyl or aryl.

$R^1$-$R^3$, and $R^5$ are independently H, alkyl, acyl, allyl, vinyl, $SiR_3$ (R in this context may be alkyl or a combination of alkyl and aryl)

$R^2$, $R^3$ may be C=O (cyclic carbonate)

$R^4$ may be H, alkyl, heteroalkyl, cycloalkyl, heterocycloalkyl, vinyl, allyl, acyl, aryl, heteroaryl, alkylaryl, alkylheteroaryl; it will be understood by the skilled artisan that more complex residues may be represented by this position, for example mono- or oligofunctional moieties or even pharmacophores or otherwise a desired activity causing assembly of chemical building blocks);

Q=—(C=O)— or —N($CH_3$)—$CH_2$—;

or a pharmaceutically acceptable salt thereof.

In another embodiment, the invention provides compounds represented by the formula (Formula XVIII):

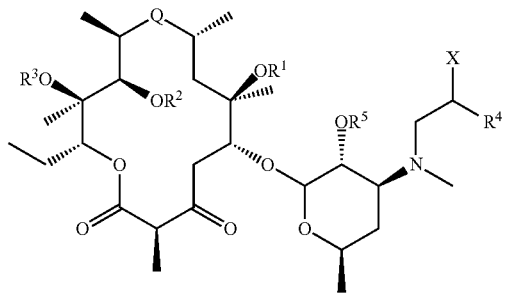

wherein
X=H or OH or NH(R), in which R is H, lower alkyl or aryl.
$R^1$-$R^3$, and $R^5$ are independently H, alkyl, acyl, allyl, vinyl, $SiR_3$ (R in this context may be alkyl or a combination of alkyl and aryl)

$R^2$, $R^3$ may be C=O (cyclic carbonate)

$R^4$ may be may be independently H, alkyl, heteroalkyl, cycloalkyl, heterocycloalkyl, vinyl, allyl, acyl, aryl, heteroaryl, alkylaryl, alkylheteroaryl; or $R^4$ and $R^{4'}$ may independently be H, alkyl, heteroalkyl, cycloalkyl, heterocycloalkyl, vinyl, allyl, acyl, aryl, heteroaryl, alkylaryl, alkylheteroaryl; or $R^4$ may also represent more complex residues, for example mono- or oligofunctional moieties (polyamines, bicyclic systems, peptides amines, halogenides, sulphonic esters, acetals, esters, aldehydes, sulfones, sulfonamides, lactones, boronates, silicates, hydroxylamines, alcohols or any type of heterocycle such as imidazoles, thiazoles pyrimidines and combinations thereof), pharmacophores (e.g. sterols, hormones, peptide analogs, nucleosides, anti-inflammatory structures, protease inhibitors, kinase inhibitors) or specifically reactive functions (hydrazines, amino groups, 1,3-dicarbonyl or carboxyl groups, bromoalkyl and bromoaryl groups) that may be conveniently reacted with reagents to form heterocyclic residues or cyclic or heterocyclic assemblies);

Q=—(C=O)— or —N($CH_3$)—$CH_2$—;

or a pharmaceutically acceptable salt thereof.

Methods of Treatment

In another aspect, this invention features a method for treating an inflammatory, viral, bacterial, cardio-vascular modulators, metabolic or immune disorder. The method includes administering to a subject in need thereof an effective amount of a compound described herein. Optionally, the method includes co-usage with other anti-inflammatory agents or therapeutic agents. Without wishing to be bound by any particular theory, it is believed that the use of the compounds described herein improves therapy at least in part because of the preferential access of the compounds to immune cells including neutrophils, monocytes, eosinophils, macrophage, alveolar macrophage, B and T-lymphocytes, NK cells, giant cells, Kupfer cells, glial cells, and similar target cells.

Compounds prepared according to the methods described above are exemplified herein and examples of their biological activity are recorded in Table 3. From these data, it can be seen that the various derivatives are able to modulate the synthesis or release of cytokines or small molecule signaling substances such as NO. These effects are dose responsive and vary with structure. For example, the modulation of the neutrophil migration factor KC by a compound of the invention (see Example 31) has an $EC_{50}$ in the order of 100 nM.

In one embodiment, the invention provides a method of treating an inflammatory disorder, the method including administering to a subject in need thereof an effective amount of a compound of the invention, e.g., a compound of one of Formulas I-XVIII (more preferably Formula III or Formula X), such that the inflammatory disorder is treated.

In another embodiment, the invention provides a method of treating an infectious disease, the method including administering to a subject in need thereof an effective amount of a compound of the invention, e.g., a compound of one of Formulas I-XVIII (more preferably Formula III or Formula X), such that the infectious disease is treated.

In another embodiment, the invention provides a method of treating cancer, the method including administering to a subject in need thereof an effective amount of a compound of the invention, e.g., a compound of one of Formulas I-XVIII (more preferably Formula III or Formula X), such that the cancer is treated.

In another embodiment, the invention provides a method of treating allergy, the method including administering to a subject in need thereof an effective amount of a compound of the invention, e.g., a compound of one of Formulas I-XVIII (more preferably Formula III or Formula X), such that the allergy is treated.

In another embodiment, the invention provides a method of treating an immune disorder, the method including administering to a subject in need thereof an effective amount of a compound of the invention, e.g., a compound of one of Formulas I-XVIII (more preferably Formula III or Formula X), such that the immune disorder is treated.

In another embodiment, the invention provides a method of treating a hematopoietic disorder, the method including administering to a subject in need thereof an effective amount of a compound of the invention, e.g., a compound of one of Formulas I-XVIII (more preferably Formula III or Formula X), such that the hematopoietic disorder is treated.

In another embodiment, the invention provides a method of treating a metabolic disease, the method including administering to a subject in need thereof an effective amount of a compound of the invention, e.g., a compound of one of Formulas I-XVIII (more preferably Formula III or Formula X), such that the metabolic disease is treated.

In another embodiment, the invention provides a method of treating a metabolic disease, the method including administering to a subject in need thereof an effective amount of a compound of the invention, e.g., a compound of one of Formulas I-XVIII (more preferably Formula III or Formula X), such that the metabolic disease is treated.

Determination of a therapeutically effective amount or a prophylactically effective amount of the compound of the invention of the invention, can be readily made by the physician or veterinarian (the "attending clinician"), as one skilled in the art, by the use of known techniques and by observing results obtained under analogous circumstances. The dosages may be varied depending upon the requirements of the patient in the judgment of the attending clinician; the severity of the condition being treated and the particular compound being employed. In determining the therapeutically effective amount or dose, and the prophylactically effective amount or dose, a number of factors are considered by the attending clinician, including, but not limited to: the specific disease or disorder involved; pharmacodynamic characteristics of the particular agent and its mode and route of administration; the desired time course of treatment; the species of subject; its size, age, and general health; the specific disease involved; the degree of or involvement or the severity of the disease; the response of the individual patient; the particular compound administered; the mode of administration; the bioavailability characteristics of the preparation administered; the dose regimen selected; the kind of concurrent treatment (i.e., the interaction of the compound of the invention with other co-administered therapeutics); and other relevant circumstances.

Treatment can be initiated with smaller dosages, which are less than the optimum dose of the compound. Thereafter, the dosage may be increased by small increments until the optimum effect under the circumstances is reached. For convenience, the total daily dosage may be divided and administered in portions during the day if desired.

Pharmaceutical Compositions

The present invention also features a pharmaceutical composition including at least one compound of this invention and a pharmaceutically acceptable carrier. Optionally, the pharmaceutical composition includes one or more other therapeutic agents.

This invention further features a method for making any of the compounds described above. The method includes taking any intermediate compound delineated herein, reacting it with any one or more reagents to form a compound of this invention including any processes specifically delineated herein.

Also within the scope of this invention are a pharmaceutical composition including one or more of the compounds of this invention, or a pharmaceutically acceptable salt thereof, together with a pharmaceutically acceptable excipient. The pharmaceutical compositions, optionally including one or more other therapeutic agents, can be used in treating various diseases, e.g., as described above. The invention also features the use of a compound or composition of the invention for the manufacture of a medicament for the treatment of disease.

To practice the method of treating a disease or disorder, the compounds of this invention can be administered to a patient, for example, in order to treat a disease described above. The compound can, for example, be administered in a pharmaceutically acceptable carrier such as physiological saline, in combination with other therapeutic agents, and/or together with appropriate excipients. The compound described herein can, for example, be administered by injection, intravenously, intraarterially, subdermally, intraperitoneally, intramuscularly, or subcutaneously; or orally, buccally, nasally, transmucosally, topically, in an ophthalmic preparation, by inhalation, by intracranial injection or infusion techniques, with a dosage ranging from about 0.1 to about 20 mg/kg of body weight, preferably dosages between 10 mg and 1000 mg/dose, every 4 to 120 hours, or according to the requirements of the particular therapeutic agent. The methods herein contemplate administration of an effective amount of compound or compound composition to achieve the desired or stated effect. Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, therapeutic agent combination, the severity and course of the disease, condition or symptoms, the patient's disposition to the disease, condition or symptoms, and the judgment of the treating physician.

Pharmaceutical compositions of this invention comprise a compound of this invention or a pharmaceutically acceptable salt thereof; and any pharmaceutically acceptable carrier, adjuvant or vehicle. Such compositions may optionally comprise additional therapeutic agents. The compositions delineated herein include the compounds of the formulae delineated herein, as well as additional therapeutic agents if present, in amounts effective for achieving a modulation of a disease.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying therapeutic agent delivery systems (SEDDS) such as D-alpha-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as I-, θ-, and K-cyclodextrin, or chemically modified derivatives such as hydroxyalkylcyclodextrins, including 2- and 3-hydroxypropyl-θ-cyclodextrins, or other solubilized derivatives may also be advantageously used to enhance delivery of compounds of the formulae described herein. Oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions.

The pharmaceutical compositions of this invention may be orally administered in any orally acceptable dosage form including, but not limited to, capsules, tablets, emulsions and aqueous suspensions, dispersions and solutions. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

A suitable in vitro assay can be used to preliminarily evaluate a compound of this invention in treating a disease. In vivo screening can also be performed by following procedures well known in the art.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

The invention will be further described in the following examples. It should be understood that these examples are for illustrative purposes only and are not to be construed as limiting this invention in any manner.

EXAMPLES

Example 1

2'-deoxy-3'-dedimethylamino-2',3'-epoxyazithomycin

A suspension of 26 g of azithromycin in 17 ml of DMF was heated to 70° C. and 7.5 ml of epichlorohydrin is added. The mixture is stirred at the same temperature for 8 h. After this period another 4 ml of epichlorohydrine is added and heating and stirring continued for 12 h. After this period most of the volatiles are removed in vacuum at 60° C. The residue is treated with 100 ml of isopropanol and 50 ml of water and the slurry is transferred into a vessel containing 200 ml of water and 4 g of potassium carbonate. Precipitation occurs and the mixture is stirred at ambient temperature for 12 h to complete precipitation. The solid (about 14 g) was filtered off to yield the crude product. That product was redissolved in 80 ml of hot isopropanol and filtered. The filtrate was allowed to cool, yielding 9.5 g of the pure product.

Example 2

3'-dedimethylamino-4'-dehydroazithromycin 12 g of azithromycin 3'-N-oxide was heated in a Kugelrohr apparatus to 150-155° C. while applying a vacuum of 20 mbar. After 1 h at this temperature the flask was cooled and the clear brownish oil taken up in ethyl acetate. The solution was filtered through a pad of silica gel (20 cm×3 cm), elution with ethyl acetate. Evaporation of the solvent yielded a slightly brown solid that can be used without further purification or can be subjected to recrystalisation from hot acetonitrile. $C^{13}$-NMR: 178.4, 132.2, 126.3, 102.1, 94.8, 83.3, 77.9, 74.1, 73.5, 7.8, 69.9, 68.6, 65.3, 60.2, 49.3, 45.2, 42.2, 41.8, 36.2, 34, 6, 27.2, 26.5, 21.9, 21.4, 21.1, 20.8, 17.8, 16.1, 14.7, 14.1, 11.1, 9.1, 7.2.

Example 3

3'-dedimethylamino-4'-dehydro-3',4'-epoxyazithromycin-1-N-oxide

A solution of 3 g of the product obtained as described in example 2 in 12 ml of dichloromethane was treated with 4 g of mCPBA (75%) in several portions within 1 h. After 7 h the mixture was diluted with 70 ml of dichloromethane. The solution was washed with sodium sulfite solution, sodium carbonate solution and brine. Evaporation yielded a white solid that was used without purification.

Example 4

4'-hydroxyazithromycin 700 mg of the product obtained as described above was heated in 2 ml of dimethylamine at 75° C. for 48 h. After cooling the contained was opened and the excess dimethylamine removed in vacuum. The residue was taken up in 3 ml of methanol and heated to reflux in the presence of 300 mg of ammonium formate and 50 mg of Palladium on charcoal (10%). The methanol was evaporated and the residue was taken up in dichloromethane and filtered through silica gel, elution with ethyl acetate containing 2% of triethylamine to yield the product, Rf=0.3 [dichloromethane:isopropanol:ammonia (7 M in methanol) 20:1:1].

Example 5

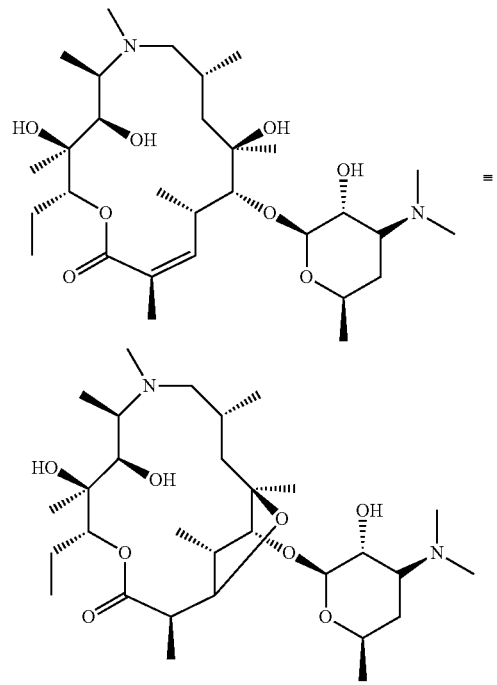

A solution of 3.0 g of azithromycin in 15 ml of dry DMF is heated together with 4 g of sodium azide to reflux for 10 h. After cooling the mixture was poured into 5% aqueous citric acid (200 ml) and then extracted with ethyl acetate (3×100 ml). The aqueous phase was treated with potassium carbonate until basic and then extracted with ethyl acetate. The organic phase was washed with brine, dried with (sodium sulfate) and concentrated under vacuum. The residue was chromatographed on silica gel, elution with chloroform:isopropanol:ammonia (solution in MeOH) 30:1:1 (Rf=0.09) to yield an off white solid. MS: 573 (M+1).

Example 6

3'-[1,4]-diazepan-1-yl-3'-desdimethylaminoazithromycin/2'-[1,4]-diazepan-1-yl-2'-dehydroxy-3'-desdimethylamino-3'-hydroxyazithromycin A solution of 150 mg of 2'-deoxy-3'-dedimethylamino-2',3'-epoxyazithomycin, prepared as in example 1, and 60 mg of homopiperazine in 3 ml of DMF is heated to 70° C. for 12 h. After cooling the mixture is partitioned between ethyl acetate and water. The ethyl acetate phase was washed several times with water and brine, dried over sodium sulfate and concentrated in vacuum to yield the crude mixture of regioisomeres in roughly the same amounts. The crude product was used without further purification.

Example 7

N-3'-(3-bromopropyl)-N-3'-desmethylazithromycin

A mixture of 3.0 g of 3'-demethylazithromycin, 4 g of potassium carbonate and 5 ml of 1,3-dibromopropane was stirred in 20 ml of DMF at 50° C. for 24 h. After cooling all volatiles were removed in vacuum and the residue partitioned between water and ethyl acetate. The organic phase was washed with brine, dried over sodium sulfate and concentrated to yield a residue that was used without further purification.

Example 8

N-3'-(4-bromobutyl)-N-3'-desmethylazithromycin

The compound was prepared in the same way as for N-3'-(3-bromopropyl)-N-3'-demethylazithromycin (example 7) by substituting 1,3-dibromopropane by 1,4-dibromobutane.

Example 9

N-3'-(6-bromohexyl)-N-3'-desmethylazithromycin

The compound was prepared in the same way as for N-3'-(3-bromopropyl)-N-3'-demethylazithromycin (example 7) by substituting 1,3-dibromopropane by 1,6-dibromohexane.

Example 10

N-3'-(3-bromopropyl)-N-3'-desmethyl-3-decladinosylazithromycin

The title compound was prepared in the same way as N-3'-(3-bromopropyl)-N-3'-demethylazithromycin (example 7) by substituting 3'-desmethylazithromycin with 3'-desmethyl-3-decladinosylazithromycin.

Example 11

N-3'-(6-bromohexyl)-N-3'-desmethyl-3-decladinosylazithromycin

The compound was prepared in the same way as N-3'-(3-bromopropyl)-N-3'-desmethylazithromycin (example 7) by substituting 3'-desmethylazithromycin with 3'-N-desmethyl-3-decladinosylazithromycin and 1,3-dibromopropane with 1,6-dibromohexane.

Example 12

N-3'-(6-aminohexyl)-N-3'-desmethyl-3-decladinosylazithromycin 120 mg of N-3'-(6-bromohexyl)-N-3'-desmethyl-3-decladinosylazithromycin (example 11) was added to 12 ml of a solution of ammonia in methanol (7 M). After stiffing for 48 h all volatiles were evaporated in vacuum and the residue partitioned between aqueous potassium carbonate and ethyl acetate. The organic phase was washed with brine, dried over sodium sulfate and concentrated to yield a residue that was used without further purification.

Example 13

N-3'-(4-aminobutyl)-N-3'-desmethylazithromycin

The compound was prepared in the same way as N-3'-(6-aminohexyl)-N-3'-desmethyl-3-decladinosylazithromycin (example 12) by substituting N-3'-(6-bromohexyl)-N-3'-desmethyl-3-decladinosylazithromycin by N-3'-(4-bromobutyl)-N-3'-desmethylazithromycin.

Example 14

N-3'-(3-hydrazinopropyl)-N-3'-desmethylazithromycin

To a solution of 4 ml of hydrazin hydrate in 15 ml of DMF was added 800 mg of N-3'-(3-bromopropyl)-N-3'-desmethylazithromycin (example 7). After stirring for 24 h at 40° C. all volatiles were removed in vacuum and the residue partitioned between aqueous potassium carbonate and ethyl acetate. The organic phase was washed with brine, dried over sodium sulfate and concentrated to yield a residue that was used without further purification.

Example 15

N-3'-glycidyl-N-3'-desmethylazithromycin

A suspension of 3 g of 3'-demethylazithromycin in 15 ml of isopropanol was stirred with 2 ml of epichlorohydrin for 24 h. All volatiles were removed then and the residue partitioned between water, potassium carbonate and ethyl acetate. The organic phase was washed with brine, dried over sodium sulfate and concentrated to yield a residue that was used without further purification.

Example 16

N-3'-glycidyl-N-3'-desmethyl-3-decladinosyl-3-dehydro-3-oxoazithromycin

The compound was prepared in the same way as for N-3'-glycidyl-N-3'-desmethylazithromycin (example 15) by substituting N-3'-glycidyl-N-3'-desmethylazithromycin for N-3'-desmethyl-3-decladinosyl-3-dehydro-3-oxoazithromycin.

Example 17

N-3'-{3-[(m-glycidyloxy)-phenoxy]-2-hydroxypropyl}-3'-N-desmethylazithromycin

A solution of 120 mg of 3'-N-desmethylazithromycin and 100 mg of resorcinol bisglycidylether in 3 ml of DMSO is heated to 100° C. for 4 h. After cooling the mixture is partitioned between ethyl acetate and water. The ethyl acetate phases are washed several times with brine, dried over sodium sulfate and concentrated in vacuum to yield a crude product that was used without further purification.

Example 18

3'-N-(3-azido-2-hydroxypropyl)-3'-N-desmethylazithromycin

A solution of 45 mg of N-3'-glycidyl-N-3'-desmethylazithromycin (example 15) in 1 ml of DMSO was treated with 30 mg of sodium azide at 70° C. for 8 h. After cooling the mixture was partitioned between ethyl acetate and water. The ethyl acetate phase was washed with brine, dried over sodium sulfate and concentrated to yield the desired product.

Example 19

N-3'-p-aminobenzyl-N-3'-desmethylazithromycin

A solution of 700 mg of N-3'-desmethylazithromycin in 5 ml of DMF is treated with 210 mg of nitrobenzylbromide and 200 mg of potassium carbonate. After 6 h the mixture was poured onto water and extracted with ethyl acetate. The organic extract was washed with brine, dried over sodium sulfate and concentrated in vacuum. The residue was used without further purification. The material was dissolved in 20 ml of methanol and stirred under an atmosphere of hydrogen in the presence of 200 mg of 3% palladium on charcoal for 2 d. The mixture was then filtered, the filtrate concentrated and the residue chromatographed on silica gel, elution with chloroform/isopropanol/ammonia (7 M in methanol) 60:1:1 to yield the desired product.

Example 20

N-3'-p-bromobenzyl-N-3'-desmethylazithromycin

A solution of 700 mg of N-3'-desmethylazithromycin in 5 ml of DMF is treated with 250 mg of p-bromobenzylbromide and 200 mg of potassium carbonate. After 6 h the mixture was poured onto water and extracted with ethyl acetate. The organic extract was washed with brine, dried over sodium sulfate and concentrated in vacuum. The residue was used without further purification

Example 21

N-3'-[3-(p-formylphenyloxy)-2-hydroxypropyl]-N-3'-desmethylazithromycin

A solution of 100 mg of N-3'-glycidyl-N-3'-desmethylazithromycin (example 15) in 3 ml of DMF was treated with 100 mg of potassium carbonate and 25 mg of p-hydroxybenzaldehyde at 50° C. for 24 h. After cooling the mixture was partitioned between water and ethyl acetate and the ethyl acetate phase was washed several times with 20% potassium carbonate solution. The organic phase was washed with brine, dried over sodium sulfate and concentrated in vacuum. The residue was used without further purification.

Example 22

N-3'-(3-amino-2-hydroxypropyl)-N-3'-desmethylazithromycin

To 10 ml of a solution of ammonia in methanol (7 M) was added 1.5 g of N-3'-desmethylazithromycin. After 24 h all volatiles were evaporated and the residue partitioned between water, potassium carbonate and ethyl acetate. The organic phase was washed with brine, dried over sodium sulfate and concentrated to yield a residue that was used without further purification.

Example 23

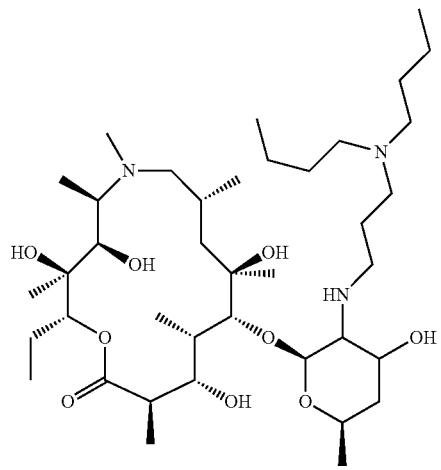

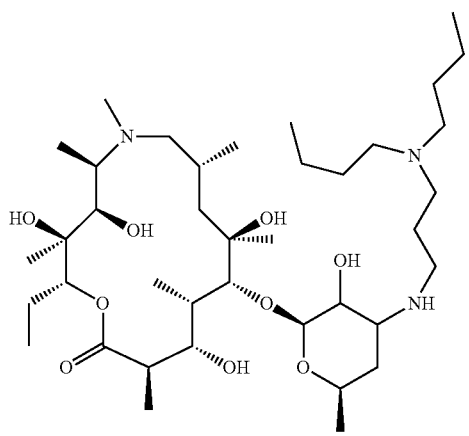

A mixture of 200 mg of the product obtained as described in example 1 together with 90 mg of aminopropyl dibutyl amine in 2 ml of isopropanol was heated for 24 h at 90° C. After cooling the mixture was poured onto water and extracted with ethyl acetate. The combined organic extracts were washed (brine,) dried (sodium sulfate) and concentrated in vacuum. The residue was taken up in 1 M hydrochloric acid and kept at ambient temperature for 2 h. After this period the ph was adjusted to >10 with potassium carbonate and the mixture was extracted with ethyl acetate. The combined organic extracts were washed (brine), dried (sodium sulfate) and concentrated in vacuum. The residue was chromatographed on silica gel, elution with chloroform/isopropanol/ammonia 20:1:1 to yield the mixture of the title compounds.

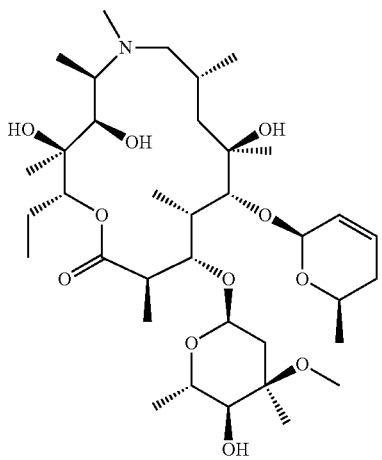 [SMILES: CC[C@H]1OC(=O)[C@H](C)[C@@H](O[C@H]2C[C@@](C)(OC)[C@@H](O)[C@H](C)O2)[C@H](C)[C@@H](O[C@H]2C=CC[C@@H](C)O2)[C@](C)(O)C[C@@H](C)CN(C)[C@H](C)[C@@H](O)[C@]1(C)O]

Example 24

A mixture of 200 mg of product obtained as described in example 1 and 2 g of triphenyl phosphine was heated in a Kugelrohr apparatus to 230° C. while applying a vacuum of about 25 mmbar. The temperature was kept for about 45 min, then the flask was cooled and the content taken up in 20 ml of ethyl acetate. The mixture was extracted with cold 5% citric acid (4×15 ml) and the combined aqueous extracts were counter washed with ethyl acetate (2×10 ml). The pH of the aqueous extracts was adjusted to >10 and the mixture was extracted with ethyl acetate. The combined organic extracts were washed (brine) dried (sodium sulfate) and concentrated in vacuum. The residue was chromatographed on silica gel, elution with chloroform/isopropanol/ammonia 40:1:1 to yield the product.

Example 25

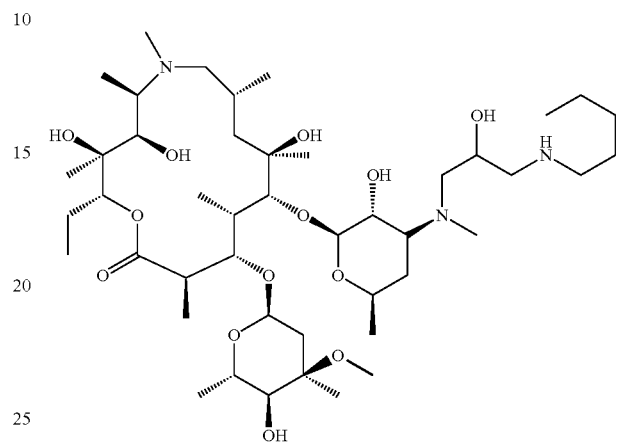

A solution of 130 mg of the 3'-N-demethyl-3'-N-(oxiranyl-methyl)-azithromycin, prepared as described above in example 15, in 1.5 ml of methanol was heated in the presence of 0.2 ml of butylamine and 0.5 ml of diisopropylethylamine for 24 h at 85° C. After cooling all volatiles were removed in vacuum and the residue used without further purification, or purified by column chromatography on silica gel.

This general procedure can be applied to various amines and other nucleophiles, as is exemplified herein below:

| Ex. num. | Nucleophile | Product | Mass detected ([M + H]+ |
|---|---|---|---|
| 21 | ammonia | (structure shown) | 808 |

-continued
| Ex. num. | Nucleophile | Product | Mass detected ([M + H]+) |
|---|---|---|---|
| 26 | spermine | 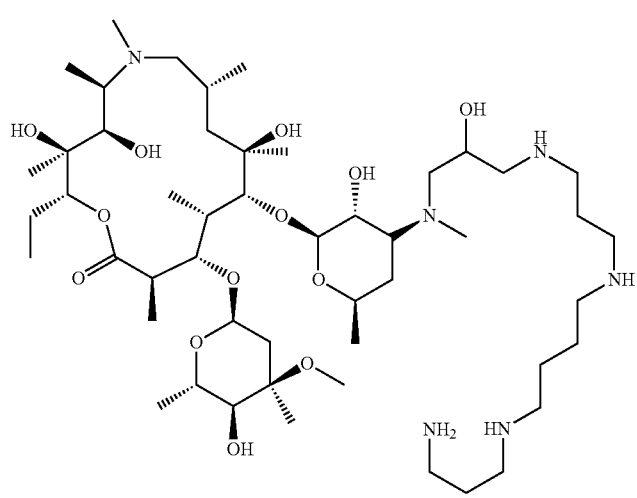 | 332* |
| | |  | |
| 27 | H-N(CH3)2 | 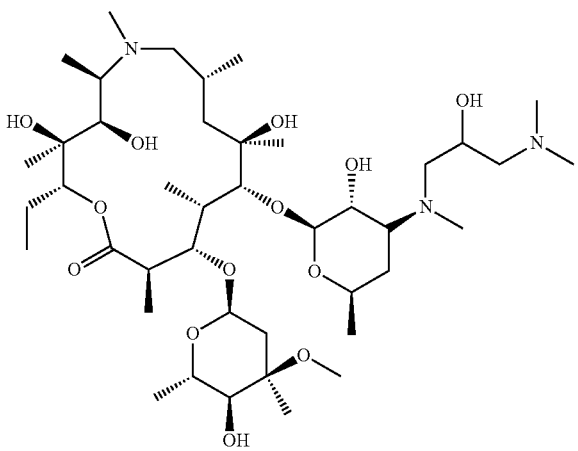 | 836 |

-continued

| Ex. num. | Nucleophile | Product | Mass detected ([M + H]+) |
|---|---|---|---|
| 28 | H₂N–⟨⟩–H₂N | (structure) | 865 |
| 29 | H₂N–⟨⟩–NH₂ | (structure) | 879 |
| 30 | H₂N–⟨⟩–BocHN | (structure) | 965 |

-continued
| Ex. num. | Nucleophile | Product | Mass detected ([M + H]+) |
|---|---|---|---|
| 31 | 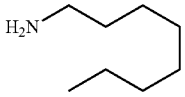 | 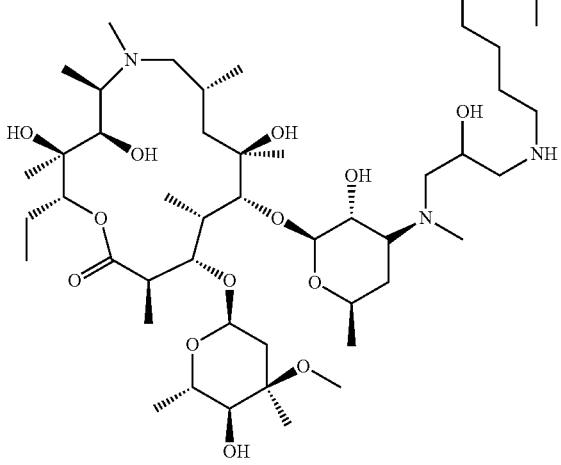 | 920 |
| 32 |  | 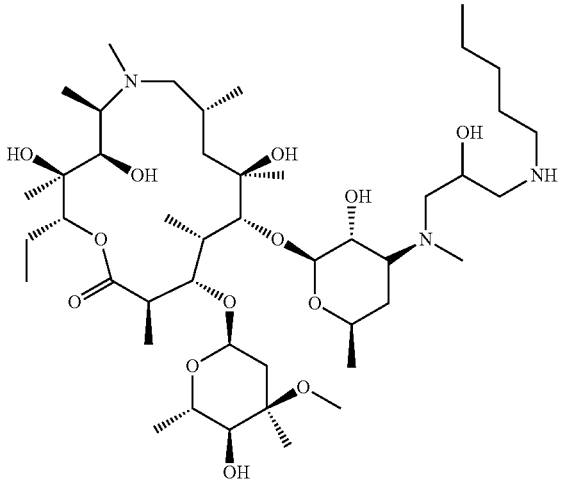 | 878 |
| 33 | 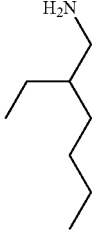 | 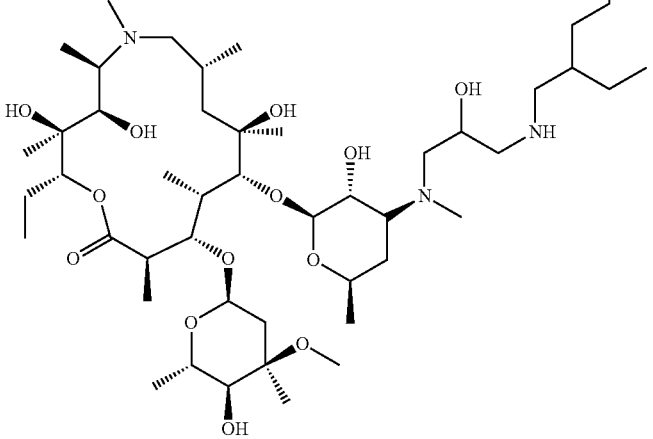 | 920 |

| Ex. num. | Nucleophile | Product | Mass detected ([M + H]+) |
|---|---|---|---|
| 34 |  | 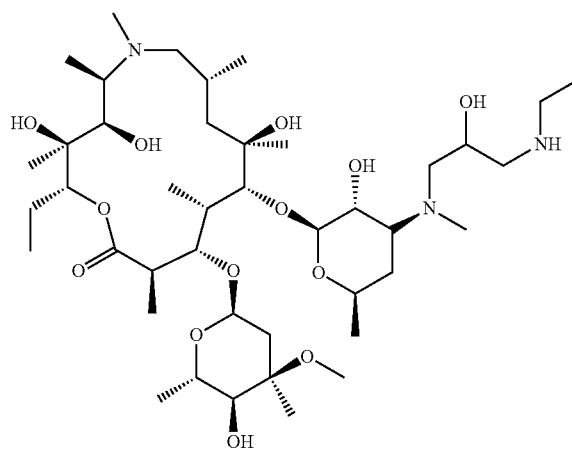 | 866 |
| 35 | 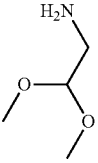 | 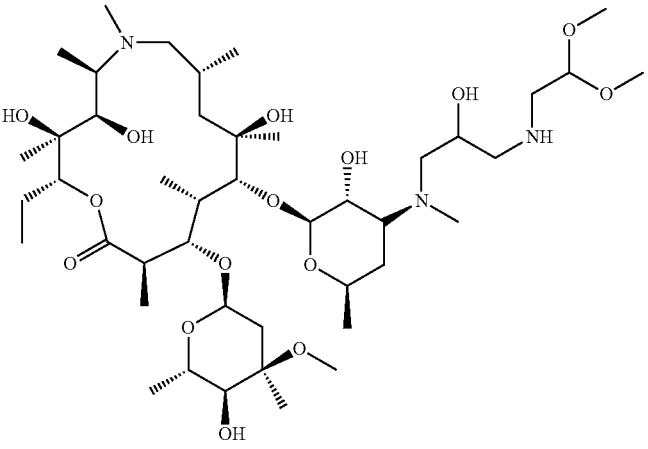 | 896 |
| 36 | 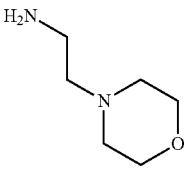 | 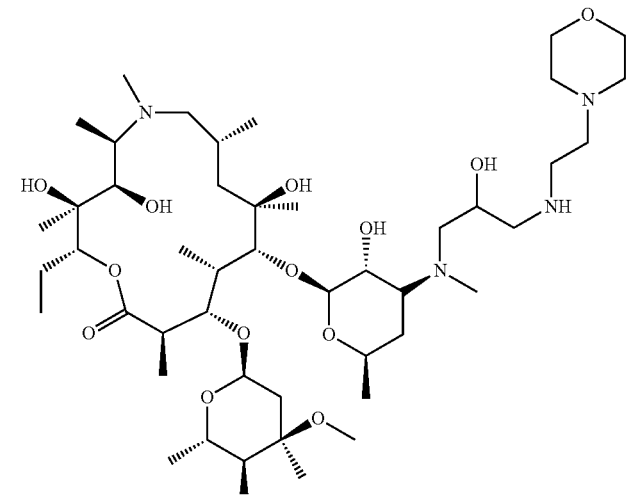 | 921 |

-continued

| Ex. num. | Nucleophile | Product | Mass detected ([M + H]+ |
|---|---|---|---|
| 37 | (morpholine) | | 878 |
| 38 | (tryptamine) | | 951 |
| 39 | (1-(3-aminopropyl)-2-pyrrolidinone) | | 933 |

-continued

| Ex. num. | Nucleophile | Product | Mass detected ([M + H]+) |
|---|---|---|---|
| 40 | (4-aminoethyl)benzenesulfonamide | | 991 |
| 41 | 2-amino-5-methylthiazole | | 905 |
| 42 | 2-amino-4-methylpyridine | | 899 |

-continued
| Ex. num. | Nucleophile | Product | Mass detected ([M + H]+) |
|---|---|---|---|
| 43 | 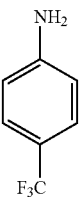 | 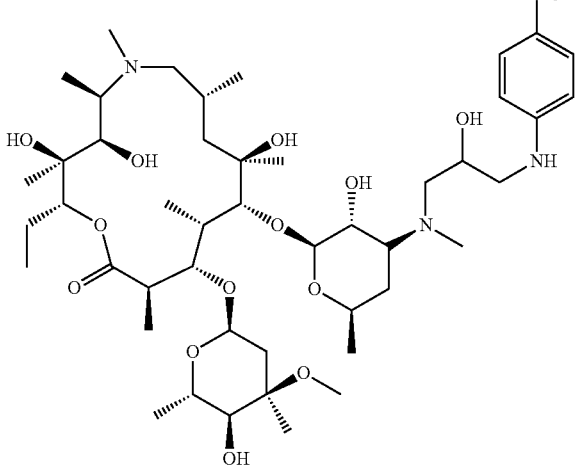 | 952 |
| 44 | 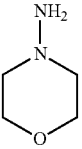 | 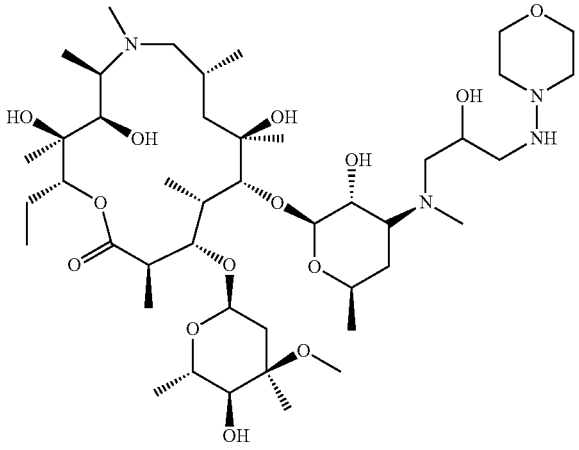 | 893 |
| 45 | 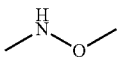 | 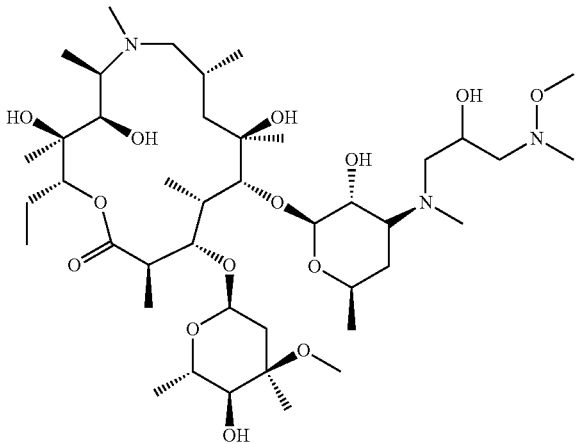 | 852 |

| Ex. num. | Nucleophile | Product | Mass detected ([M + H]+) |
|---|---|---|---|
| 46 | 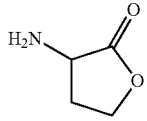 | 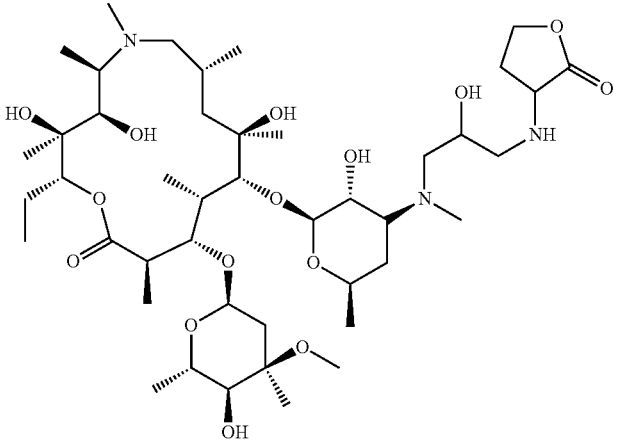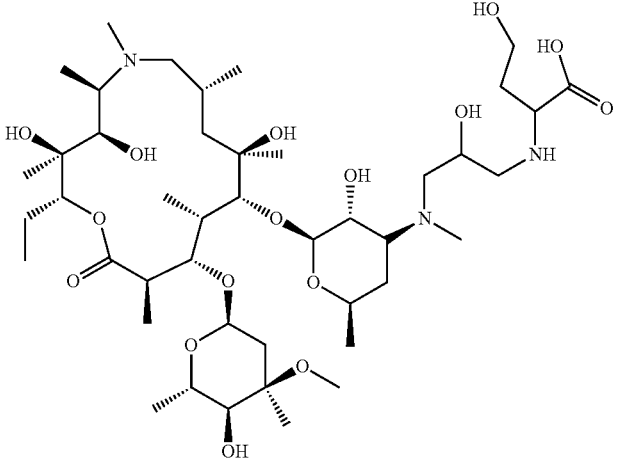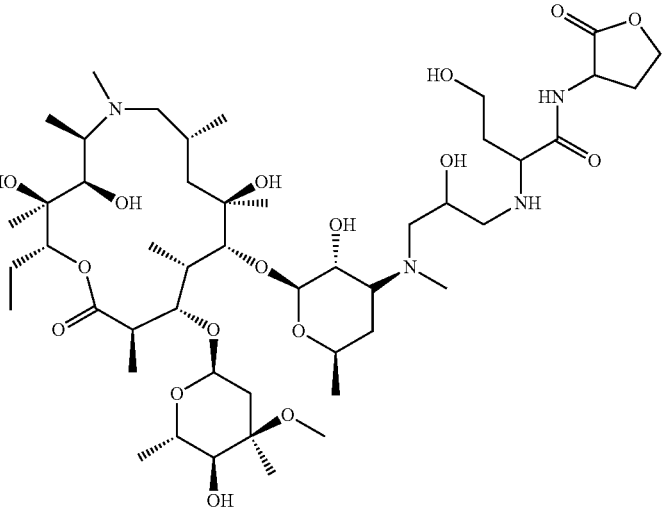 | 892, 910, 993 |

-continued
| Ex. num. | Nucleophile | Product | Mass detected ([M + H]+ |
|---|---|---|---|
| 47 | 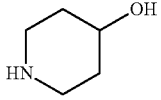 | 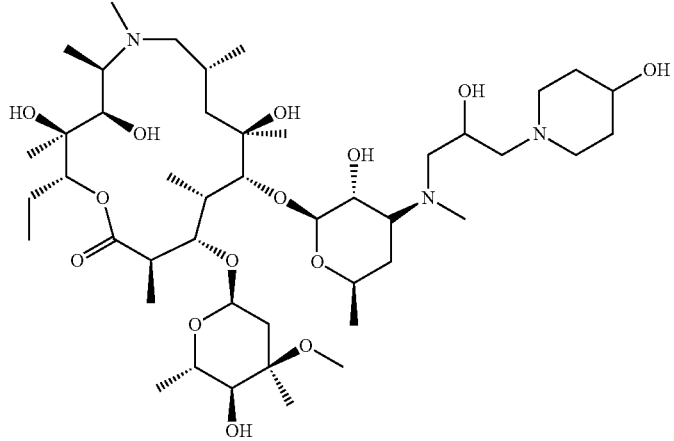 | 892 |
| 48 | 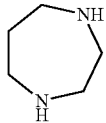 | 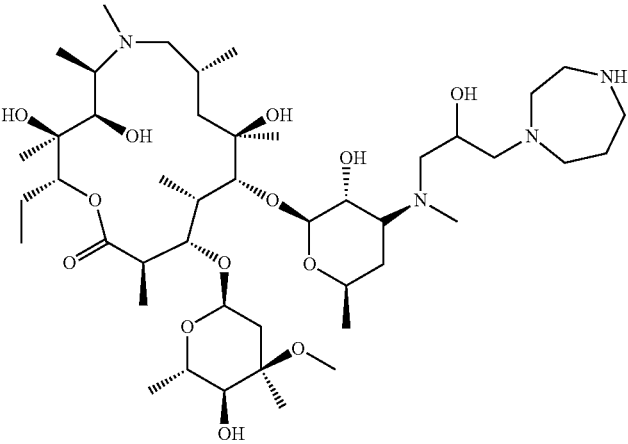 | 891 |
| 49 | 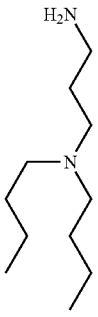 | 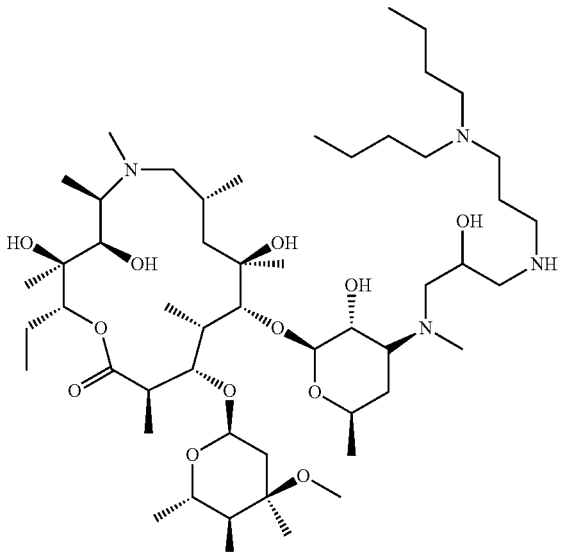 | 977 |

-continued
| Ex. num. | Nucleophile | Product | Mass detected ([M + H]+) |
|---|---|---|---|
| 50 | 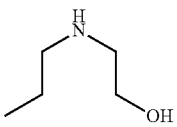 | 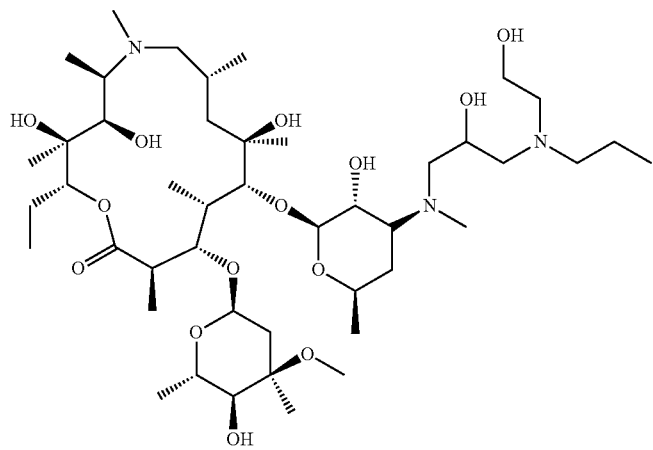 | 894 |
| 51 | 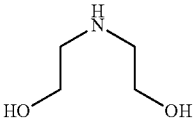 | 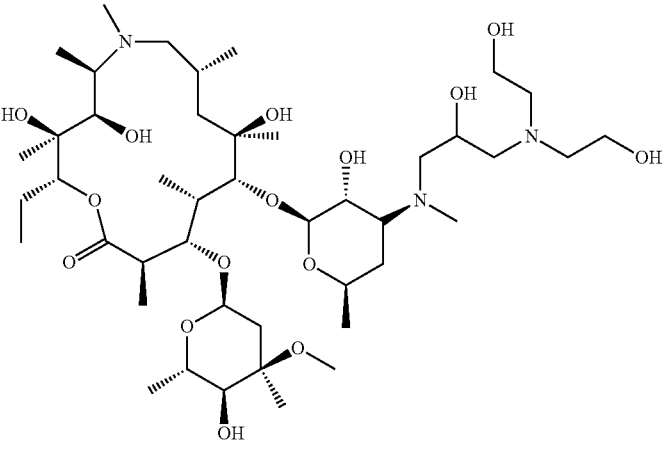 | 896 |
| 52 | 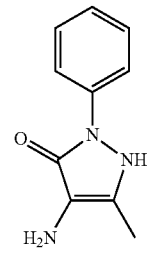 | 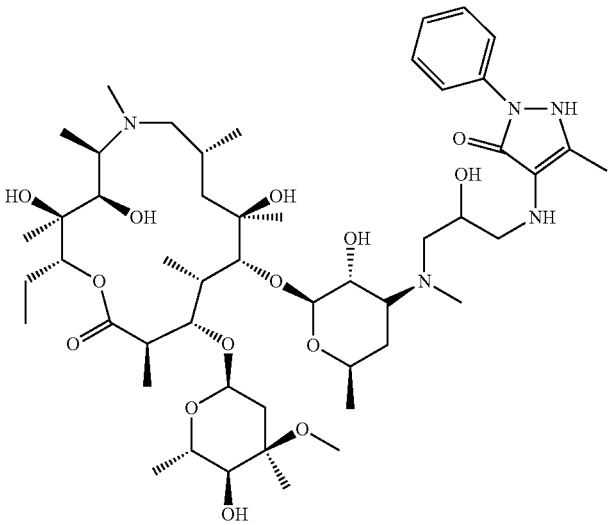 | 980 |

-continued

| Ex. num. | Nucleophile | Product | Mass detected ([M + H]+ |
|---|---|---|---|
| 53 | HO-C(CH₃)(CH₂OH)-NH₂ | (structure) | 896 |
| 54 | pyrrolidine (NH) | (structure) | 862 |
| 55 | 1-amino-2-propanol | (structure) | 866 |

-continued
| Ex. num. | Nucleophile | Product | Mass detected ([M + H]+ |
|---|---|---|---|
| 56 | 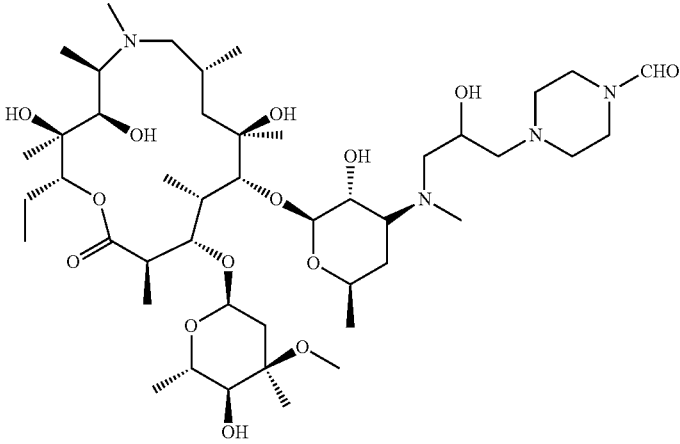 | | 905 |
| 57 | 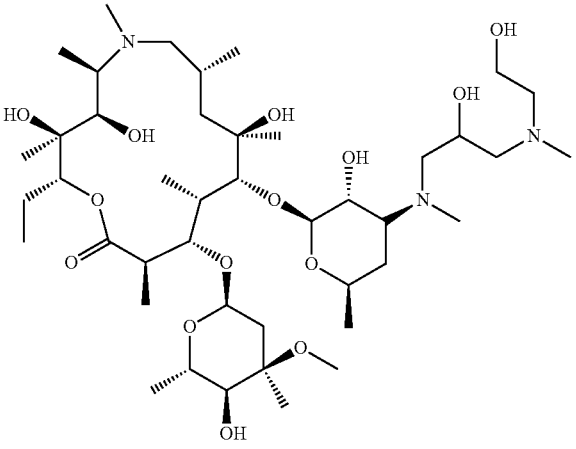 | | 866 |
| 58 | ⁻CN | 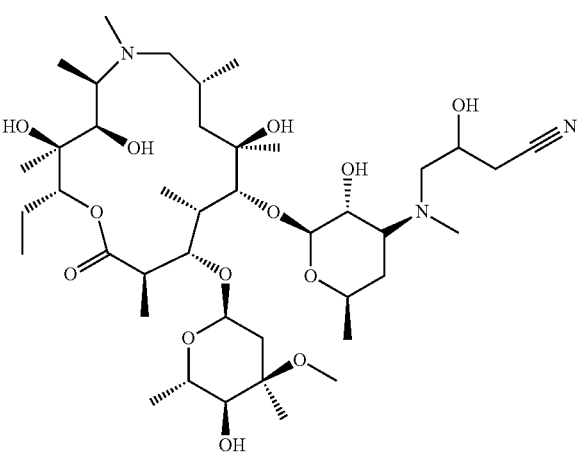 | 818 |

-continued
| Ex. num. | Nucleophile | Product | Mass detected ([M + H]+ |
|---|---|---|---|
| 59 | 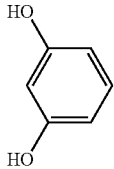 | 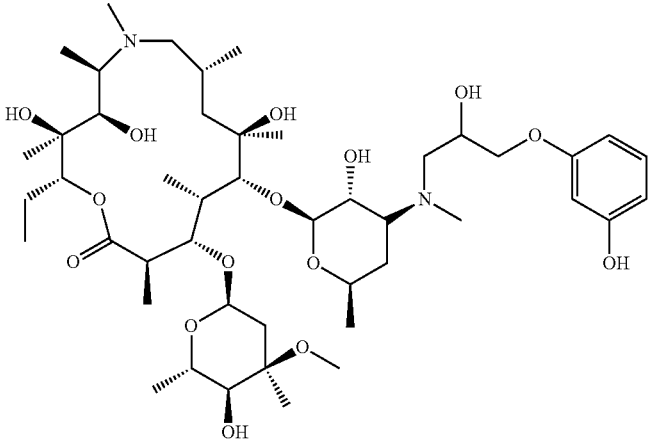 | 901 |
| 60 | 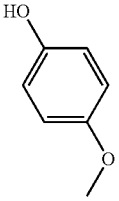 | 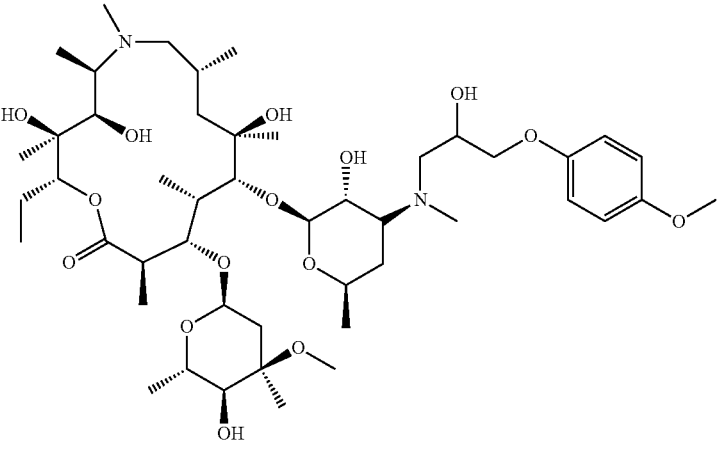 | 915 |
| 61 | 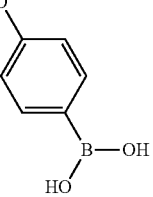 | 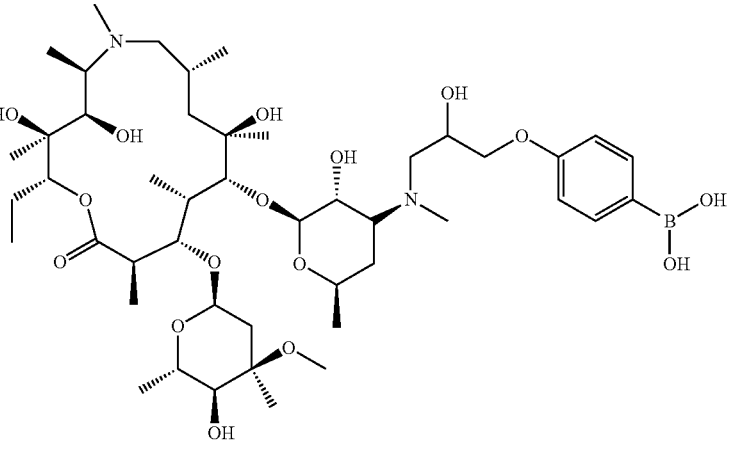 | 929 |

-continued

| Ex. num. | Nucleophile | Product | Mass detected ([M + H]+ |
|---|---|---|---|
| 62 | (4-hydroxy methyl benzoate) | | 943 |
| 63 | (N-Boc-glycine) | | 484** |
| 64 | (quinoline-3-carboxylic acid) | | 483** |

-continued

| Ex. num. | Nucleophile | Product | Mass detected ([M + H]+) |
|---|---|---|---|
| 65 | (isoquinoline-1-carboxylic acid) | | 483** |
| 66 | (4-fluorobenzoic acid) | | 466** |

\* = [M + 3H]³⁺

\*\* = [M + 2H]²⁺

This procedure may also be applied to other 3'-N-demethyl-3'-N-(oxiranylmethyl) macrolide derivatives, i.e. 3'-N-demethyl-3'-N-(oxiranylmethyl)-erythromycin (example 67, see below) or N-3'-glycidyl-N-3'-desmethyl-3-decladinosyl-3-dehydro-3-oxoazithromycin (See, e.g., Example 16).

Example 67

3'-N-demethyl-3'-N-(oxiranylmethyl)erythromycin

The compound was synthesised the same way as for N-3'-glycidyl-N-3'-desmethylazithromycin by substituting 3'-N-desmethylazithromycin with 3'-N-desmethylerythromycin. This includes, but is not limited to the following examples:

| Ex. num. | Nucleophile | Product | Mass detected ([M + H − H₂O]⁺) |
|---|---|---|---|
| 68 | 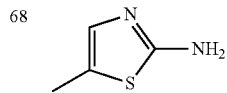 | 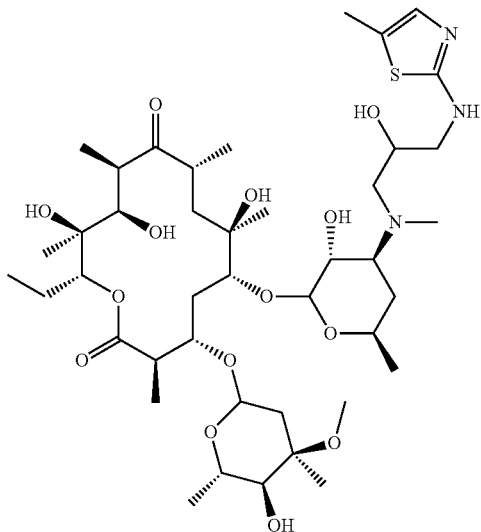 [SMILES: CC[C@H]1OC(=O)[C@H](C)[C@@H](OC2C[C@@](C)(OC)[C@@H](O)[C@H](C)O2)C[C@@H](OC2O[C@H](C)C[C@H](N(C)CC(O)CNc3ncc(C)s3)[C@H]2O)[C@](C)(O)C[C@@H](C)C(=O)[C@H](C)[C@@H](O)[C@]1(C)O] | 858 |
| 69 | 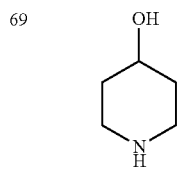 | 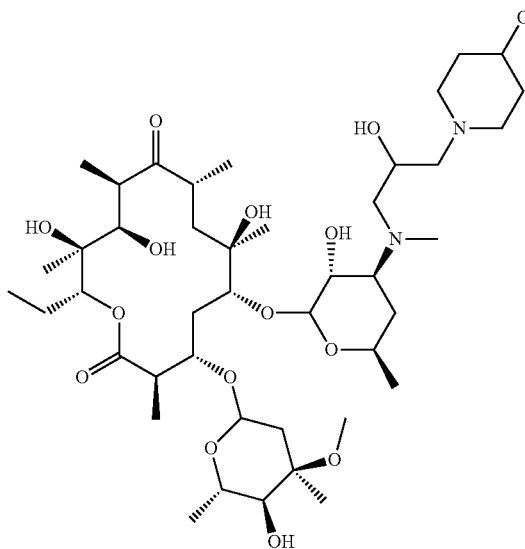 | 845 |

-continued

| Ex. num. | Nucleophile | Product | Mass detected ([M + H − H$_2$O]$^+$) |
|---|---|---|---|
| 70 | H$_2$N-CH$_2$-CH(OMe)$_2$ | | 849 |
| 71 | Boc-NH-CH$_2$-COOH | | 917 |
| 72 | 4-C$_8$H$_{17}$-C$_6$H$_4$-OH | | 948 |

-continued

| Ex. num. | Nucleophile | Product | Mass detected ([M + H − H₂O]⁺) |
|---|---|---|---|
| 73 | 1,3-dihydroxybenzene | | 852 |
| 74 | 4-(trifluoromethyl)aniline | | 903 |
| 75 | quinoline-3-carboxylic acid | | 804* |

| Ex. num. | Nucleophile | Product | Mass detected ([M + H − H₂O]⁺) |
|---|---|---|---|
| 76 | HO-C(=O)-C₆H₄-F (4-fluorobenzoic acid) | (azithromycin derivative structure) | 386** |

\* = [M + H]⁺,

\*\* = [M + 2H]²⁺

Example 77

N-3'-(4,4-dicyanobutyl)-N-3'-desmethylazithromycin

To a solution of 150 mg malononitrile and 250 mg of potassium t-butoxide in 6 ml of DMSO was added 150 mg of N-3'-(3-bromopropyl)-N-3'-desmethylazithromycin (example 7). The mixture was stirred for 12 h and then poured onto ice. The mixture was extracted with ethyl acetate and the organic extract was washed with brine, dried over sodium sulfate and concentrated in vacuum. The residue was chromatographed on silica gel, elution with chloroform/isopropanol/ammonia (7 M in methanol) 40:1:1 to yield the desired compound.

Example 78

N-3'-(7-,7-dimethoxycarbonylheptyl)-N-3'-demethyl-3-decladinosylazithromycin To a solution of 150 mg dimethyl malonate and 220 mg of potassium t-butoxide in 6 ml of DMSO was added 150 mg of N-3'-(6-bromohexyl)-N-3'-demethyl-3-decladinosylazithromycin (example 11). The mixture was stirred for 12 h and then poured onto ice. The mixture was extracted with ethyl acetate and the organic extract was washed with brine, dried over sodium sulfate and concentrated in vacuum. The residue was chromatographed on silica gel, elution with chloroform/isopropanol/ammonia (7 M in methanol) 40:1:1 to yield the desired compound.

Example 79

N-3'-(5-,5-dimethoxycarbonylpentyl)-N-3'-desmethylazithromycin

The compound was prepared in the same way as for N-3'-(7-,7-dimethoxycarbonylheptyl)-N-3'-demethyl-3-decladinosylazithromycin (example 78) by substituting N-3'-(6-bromohexyl)-N-3'-demethyl-3-decladinosylazithromycin for N-3'-(4-bromobutyl)-N-3'-desmethylazithromycin.

Example 80

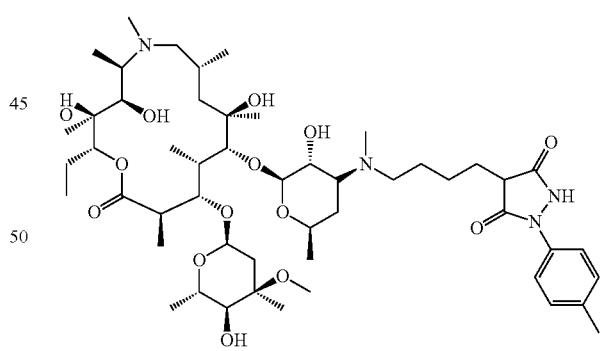

To a mixture of 50 mg of p-hydrazinotoluene hydrochloride and 50 mg of potassium carbonate in 2 ml of ethanol was added 120 mg of N-3'-(5-,5-dimethoxycarbonylpentyl)-N-3'-desmethylazithromycin (example 79). The mixture was heated to 70° C. for 8 h. After cooling the mixture was partitioned between ethyl acetate and 5% potassium carbonate solution. The combined ethyl acetate extracts were washed with brine, dried over sodium sulfate and concentrated in vacuum. The residue was chromatographed on silica gel; elution with chloroform/isopropanol/ammonia (7 M in methanol) 30:1:1 gave the desired product.

Example 81

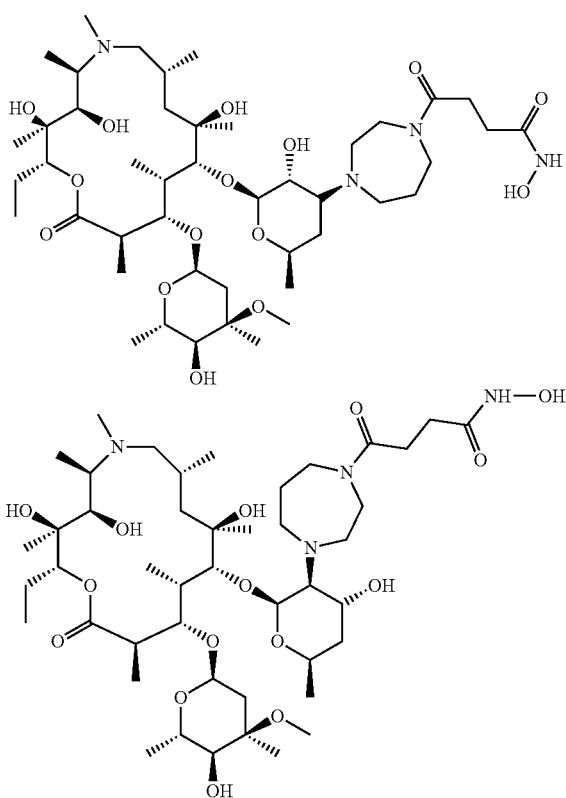

120 mg of the mixture of 3'[1,4]-diazepaN-1-yl-3'-desdimethylaminoazithromycin/2'-[1,4]-diazepaN-1-yl-2'-dehydroxy-3'-desdimethylamino-3'-hydroxaazithromycin (example 6) was dissolved in 3 ml of DMF. 50 mg of succinic acid monomethylester and 50 mg of EDCI was added. After 5 h the mixture was partitioned between water and ethyl acetate and the organic phase was washed several times with 5% potassium carbonate solution, dried over sodium sulfate and concentrated in vacuum. The residue was taken up in 2 ml of methanol. 50 mg of hydroxylamine hydrochloride and 50 ml of triethylamine was added and the mixture heated to 50° C. for 4 h. After cooling all volatiles were removed and the residue partitioned between ethyl acetate and water. The organic phase was washed with brine, dried over sodium sulfate and concentrate in vacuum to yield the crude mixture of regioisomeric products.

Example 82

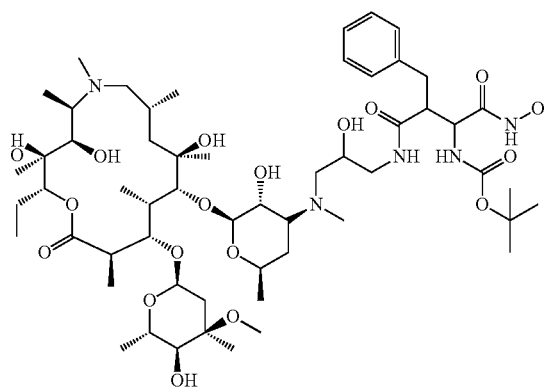

A solution of 70 mg of N-3'-(3-amino-2-hydroxypropyl)-N-3'-desmethylazithromycin (example 21) and 40 mg of 2-benzyl-3-tert-butoxycarbonylamino-succinic acid 4-methyl ester in 2 ml of DMF was treated with 100 mg of diisopropylcarbodiimide and 30 mg of hydroxysuccinic imide. After 12 h the mixture was poured onto water and extracted with ethyl acetate. The organic extract was washed with brine, dried over sodium sulfate and concentrated in vacuum. The residue was chromatographed on silica gel, elution with chloroform/isopropanol/ammonia (7 M in methanol) 30:1:1 to yield the intermediary methylester that was heated afterwards with a mixture of 2 ml of methanol and 2 ml of a 50% solution of hydroxylamine in water under argon to 60° C. for 24 h. Removal of all volatiles gave the desired product.

Example 83

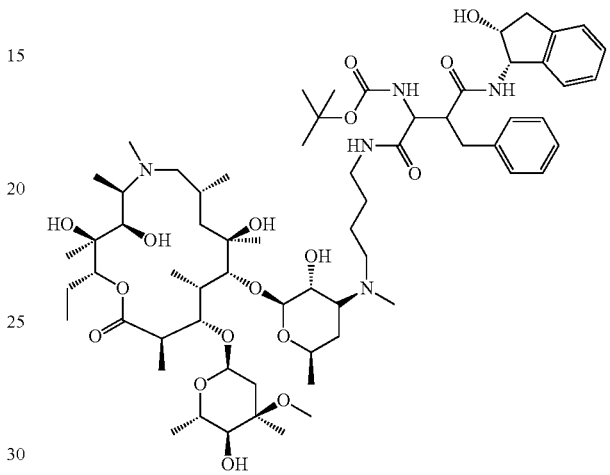

A solution of 120 mg of N-3'-(4-aminobutyl)-N-3'-desmethylazithromycin (example 13), 40 mg of hydroxysuccinic imide and 90 mg of 3-benzyl-2-tert-butoxycarbonylamino-N-(2-hydroxy-indaN-1-yl)-succinamic acid in 2 ml of DMF was treated with 70 mg of EDCI at 0° C. The mixture was stirred at the same temperature for 2 h and then allowed to stir at ambient temperature for 12 h. The mixture was partitioned between ethyl acetate and aqueous potassium carbonate solution and the organic extracts are washed with brine, dried over sodium sulfate and then concentrated in vacuum. The residue was chromatographed on silica gel, elution with chloroform/isopropanol/ammonia (7 M in methanol) 15:1:1 to yield the desired product.

Example 84

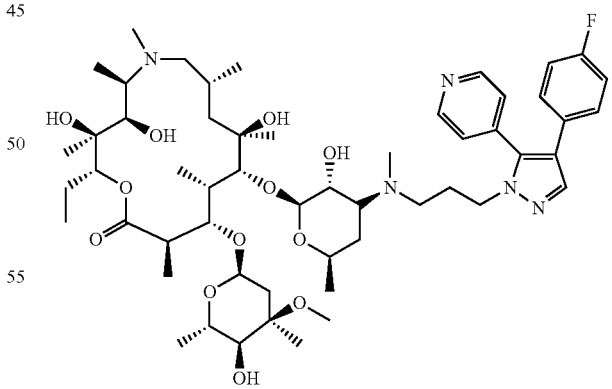

To a solution of 90 mg of 3-dimethylamino-2-(4-fluorophenyl)-1-pyridiN-4-yl-propenone in 5 ml of ethanol was added 210 mg of N-3'-(3-hydrazinopropyl)-N-3'-desmethylazithromycin (example 14). The mixture was heated to 70° C. for 12 h and then all volatiles were removed in vacuum. The residue was chromatographed on silica gel, elution with chloroform/isopropanol/ammonia (7 M in methanol) 40:1:1 to yield the desired compound.

Example 85

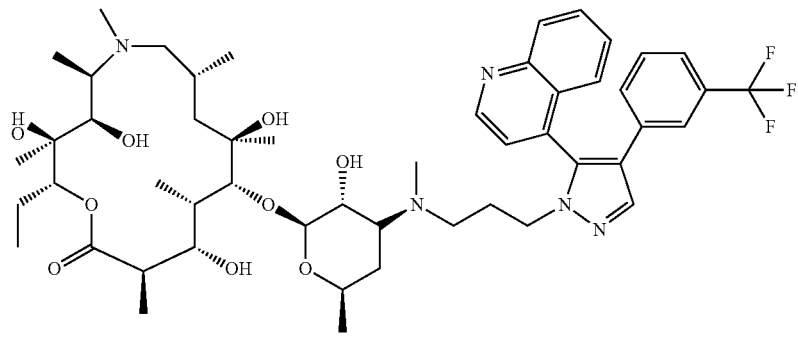

To a solution of 90 mg of 3-dimethylamino-2-quinoliN-4-yl-1-(3-trifluoromethyl-phenyl)-propenone in 4 ml of ethanol was added 180 mg of N-3'-(3-hydrazinopropyl)-N-3'-demethyl-3-decladinosylazithromycin (example 14). The mixture was heated to 70° C. for 12 h and then all volatiles were removed in vacuum. The residue was chromatographed on silica gel, elution with chloroform/isopropanol/ammonia (7 M in methanol) 40:1:1 to yield the desired compound.

Example 86

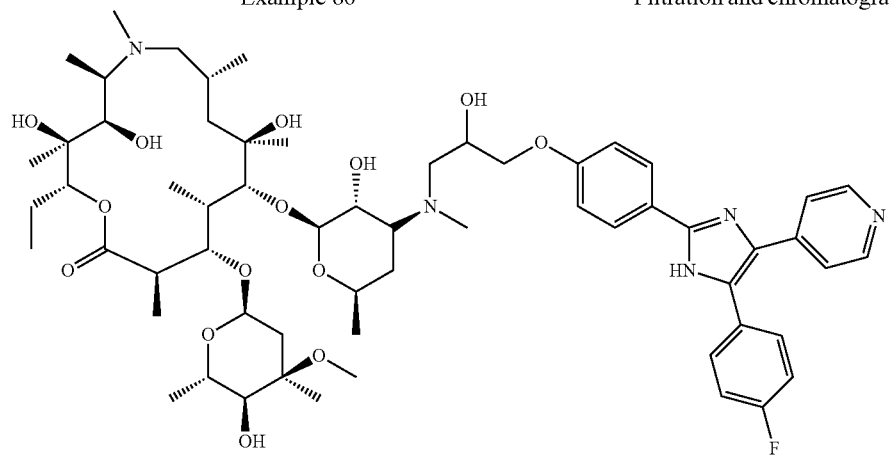

A solution of 80 mg of N-3'-[3-(p-formylphenyloxy)-2-hydroxypropyl]-N-3'-desmethylazithromycin (example 21) in 2 ml of acetic acid was heated in the presence of 200 mg of ammonium acetate and 50 mg of 1-(4-fluoro-phenyl)-2-pyridiN-4-yl-ethane-1,2-dione 1-oxime for 6 h at 60° C. After cooling most of the acetic acid was removed in vacuum and the residue partitioned between ethyl acetate and 15% potassium carbonate solution. The combined ethyl acetate extracts were washed with brine, dried over sodium sulfate and concentrated in vacuum. The residue was dissolved in methanol and hydrogenated for 48 h under an atmosphere of hydrogen in the presence of 100 mg of 3% palladium on charcoal. Filtration and chromatography of the concentrated filtrate on silica gel, elution with chloroform/isopropanol/ammonia (7 M in methanol) 20:1:1 gave the desired product.

Example 87

To a mixture of 100 mg of 4-(4-Fluoro-phenyl)-5-pyridiN-4-yl-1,3-dihydro-imidazole-2-thione and 100 mg of potassium carbonate in 2 ml of DMSO was added 100 mg of N-3'-(3-bromopropyl)-N-3'-desmethylazithromycin (example 7). The mixture was heated to 50° C. for 12 h and after cooling poured onto ice. Extraction with ethyl acetate, washing with brine, drying over sodium sulfate and concentration yielded a residue that was chromatographed on silica gel; elution with chloroform/isopropanol/ammonia (7 M in methanol) 20:1:1 to give the desired product.

Example 88

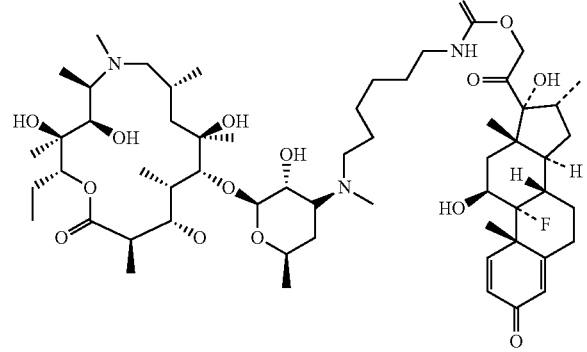

To a solution of 50 mg of dexamethasone and 20 ul of triethylamine in 2 ml of THF was added at 0° C. 25 mg of nitrophenyl chloroformate. After 1 h at this temperature 100 mg of N-3'-(6-aminohexyl)-N-3'-desmethyl-3-decladinosylazithromycin (example 12) was added and the mixture allowed standing for 2 h at ambient temperature. All volatiles were removed in vacuum and the residue partitioned between ethyl acetate and 5% potassium carbonate solution. The combined ethyl acetate extracts were washed with brine, dried over sodium sulfate and concentrated in vacuum. The residue was chromatographed on silica gel; elution with chloroform/isopropanol/ammonia (7 M in methanol) 40:1:1 gave the desired product.

Example 89

TABLE 3

Activity of various compounds from the above series in suppression of pro-inflammatory responses in isolated cells.

| Macrocycle | Side chain | IFNg (% control) at 8 µM | NO (% control) at 8 µM | Potency in NO suppression vs. Dexamethasone | Example |
|---|---|---|---|---|---|
| desmethyl erythromycin | | 6.3 | 37.1 | | |
| Dexamethasone | | 4.3 | 3.4 | | |
| A | aminocaprylic acid | | | 0.5 | |
| A | Spermine | 3.5 | 4.7 | | 26 |
| A | aminoacetaldehyde dimethylacetal | | | 0.5 | 35 |
| A | aminomethylthiazole | | | 0.5 | 41 |
| A | rearrangment of 2-amino-butyrolactone | | | 0.5 | 46 |
| A | butylene diamine | | | 0.6 | 29 |
| descladinosyltetraacetal azithromycin | | | | 0.6 | no ex |
| A | Octylamine | 4.4 | 4.7 | | 31 |
| A | amylamine | 3.7 | 6.8 | | 32 |
| A | 2-ethylhexylamine | 3.8 | 3.2 | | 33 |
| A | 3-(di-N-butylamino)propylamine | 4.3 | 48.2 | | 49 |
| A | 2-propylaminoethanol | 4.0 | 3.9 | | 50 |
| A | 4-methyl-pyridine-2-amine | | | 0.8 | 42 |
| A | Trifluoromethylaniline | 5.6 | 40.5 | | 43 |
| A | piperazine-1-carbaldehyde | | | 0.6 | 56 |
| A | aminoethanol | | | 0.5 | no ex |
| B | | 6.0 | 70.0 | | 67 |
| B | 5-methyl-thiazole-2-ylamine | 4.3 | 2.9 | | 68 |
| A | 2,2-dimethoxyethylamine | | | 0.5 | 35 |
| A | piperidine-4-ol | | | 0.5 | 47 |
| C | TriFaniline | 17.8 | 71.3 | | |
| C | Octylamine | 3.7 | 40.5 | | no ex |
| B | triFluoromethylaniline | 4.6 | 3.7 | | |
| B | Octylamine | 4.6 | 11.6 | | |
| B | resorcinol | 22.9 | 85.5 | | |
| B | phenol-heptane | 5.3 | 11.6 | | 72 |
| B | quinoline-3-carbolic acid | 4.9 | 35.3 | | |
| B | BOC Gly | 13.7 | 89.5 | | |
| B | isoquinoline carboxylate | 29.6 | 65.5 | | |
| B | fluorobenzoic acid | 5.3 | 37.6 | | 76 |
| B | 4-hydroxy-benzoic acid methyl ester | 19.9 | 91.3 | | |
| B | 4-methoxy phenol | 78.2 | 91.6 | | |
| B | phenol | 7.2 | 89.5 | | |
| B | OHquinadine | 4.4 | 3.9 | | |
| A | resorcinol | 96.9 | 99.2 | | 59 |
| A | phenol-heptane | 4.4 | 37.6 | | no ex |
| A | 3-quinoline | 7.2 | 23.4 | | no ex |

TABLE 3-continued

Activity of various compounds from the above series in suppression of pro-inflammatory responses in isolated cells.

| Macrocycle | Side chain | IFNg (% control) at 8 µM | NO (% control) at 8 µM | Potency in NO suppression vs. Dexamethasone | Example |
|---|---|---|---|---|---|
| A | boc glycine | 4.4 | 3.9 | | 63 |
| A | isoquinoline carboxylate | 30.9 | 77.6 | | 65 |
| A | 4-fluoro-benzoic acid | 5.0 | 41.6 | | 43 |
| A | 4-hydroxy-benzoic acid methyl ester | 5.3 | 63.4 | | 62 |
| A | methoxyphenol | 5.7 | 33.7 | | 60 |
| A | Phenol | 11.3 | 75.3 | | |
| A | boronic phenol | 15.6 | 74.2 | | 61 |
| A | OHQuinaldine | 4.4 | 5.5 | | no ex |
| D | quinolin carboxylate | 88.8 | 96.8 | | 75 |
| D | fluorobenzoate | 7.4 | 64.7 | | 76 |
| Desmethyl azithromycin | resorcinol | 4.7 | 4.7 | | no ex |

A = N-3'-glycidyl-N-3'-desmethylazithromycin (see example 15)
B = 3'-N-demethyl-3'-N-(oxiranylmethyl)erythromycin (see sample 67)
C = 2'-deoxy-3'-dedimethylamino-2',3'-epoxyazithromycin
D = Ketolide from descladinosyl-azithromycin (oxidized at 3-OH), a hemiacetal with 6-OH is formed Other Embodiments It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

CITATIONS

Alberola A., Antolin L. F., Gonzalez A. M., Laguna M. A., and Pulido F. J.; J. Heterocyclic Chem; 23; 1035; (1986).

Alberola A., Antolin L. F., Gonzalez A. M., Pulido F. J.; Base-induced Ring Cleavage of 4-Functionalized 3-Unsubstituted Isoxazoles. Synthesis of 2-Aminopyrimidines and Pyrimidine-2(3H)-thiones; Heterocycles; (1987).

Axton et al., 1992, J. Chem. Soc. Perkin Trans. I 2203 ff.

Bartlett et al., 1991, Agents and Actions, 32 10-21.

Benslay D N and Bendele A M, 1991, Agents Actions 34: 254.

Billingham et al., 1954. Proc. R. Soc. 143: 43-55.

Douthwaite S and Champney W S, 2001, J Antimicrob Chemother. 2001 September; 48 Suppl T1:1-8.

Elliot et al., 1998, J. Med. Chem. 41, 1651-1659.

Hutchins R O, Hoke D, Keogh J, Koharstki D, 1969, Sodium Borohydride in Dimethyl Sulfoxide or Sulfolane. Convenient Systems for Selective Redutions of Primary, Secondary, and Certain Tertiary Halides and Tosylates. Tetrahedron Letters, 3495-3498.

Ianaro et al., 2000, Anti-inflammatory activity of Macrolide Antibiotics. J. Pharmacol. Ex. Therapeutics. 292: 156-161.

Labro M T and Abdelghaffar H, 2001, Immunomodulation by macrolide antibiotics. J. Chemother. February; 13(1): 3-8. Review.

Labro M T, 1998, Anti-inflammatory activity of macrolides: a new therapeutic potential? J. Antimicrobial Chemother. 41, Suppl., 37-46.

Quallich L G, Greenson J, Haftel H M, Fontana R J, 2001, Is it Crohn's disease? A severe systemic granulomatous reaction to sulfasalazine in patient with rheumatoid arthritis, BMC Gastroenterol; 1(1): 8.

Schroit A J, Madsen J, Nayar R, 1986, Liposome-cell interactions: in vitro discrimination of uptake mechanism and in vivo targeting strategies to mononuclear phagocytes., Chem Phys Lipids. June-July; 40(2-4):373-93.

PATENTS AND PATENT PUBLICATIONS

| | | | |
|---|---|---|---|
| PCT03/070174 | February 2002 | Burnet et al | |
| PCT03/070173 | February 2002 | Burnet et al | |
| U.S. Pat. No. 4,328,334 | May 1982 | Kobrehel et al. | 536/7.4 |
| U.S. Pat. No. 3,478,014 | November 1969 | Djokic et al. | 536/9 |
| U.S. Pat. No. 3,652,537 | March 1972 | Massey | 536/9 |
| U.S. Pat. No. 4,988,677 | January 1991 | Franco | 536/7.1 |
| U.S. Pat. No. 5,543,400 | August 1996 | Agouridas | 514/646 |
| US2001/0053782A1 | December 2000 | Blumenkopf et al. | 514/258 |
| PCT03/070254A1 | February 2002 | Burnet et al. | |
| WO2004029067 | February 2003 | Berdik et al. | |
| WO09/963937 | July 1999 | Griffin | |
| EP0283055 | September 1988 | Carevic and Djokic | 540/467; 314/183 |
| EP0627406A1 | October 1992 | Fujita et al. | C07C 215/10 |

What is claimed is:

1. A compound represented by the formula:

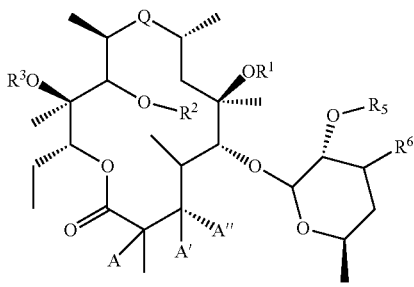

wherein

A and A' are each hydrogen or taken together form a double bond, and A" is H or OH or O-Cladinosyl;

or A=Hydrogen and A' and A" taken together represent =O;

$R^1$, $R^2$, $R^3$, and $R^5$ are independently selected from the group consisting of H, alkyl, acyl, allyl, vinyl, $SiR'_3$ in which R' is, independently for each occurrence, alkyl or aryl);

or A and A"=Hydrogen and A' and $R^1$ together represent a single bond;

$R^2$, $R^3$ may be C=O (cyclic carbonate);

$R^6$=H, OH, CN, $N_3$, $NR^8{}_2$ (in which each $R^8$ is independently H, alkyl or cycloalkyl), alkyl, cycloalkyl, —N(CH$_3$)R$^{8'}$ (in which $R^{8'}$ is H, alkyl, aryl, heteroaryl), or $SR^9$ (in which $R^9$ is H, alkyl or cycloalkyl);

Q=—N(CH$_3$)—CH$_2$—; or a pharmaceutically acceptable salt thereof.

2. A pharmaceutical composition comprising a compound of claim 1, or a pharmaceutically acceptable salt thereof, together with a pharmaceutically acceptable excipient.

3. A method of treating an inflammatory or bacterial, disorder, the method comprising administering to a subject in need thereof an effective amount of a compound of claim 1, such that the inflammatory or bacterial disorder is treated.

* * * * *